(12) United States Patent
Larkin et al.

(10) Patent No.: US 8,097,455 B2
(45) Date of Patent: Jan. 17, 2012

US008097455B2

(54) SYSTEM AND METHOD FOR FORMING SKELETAL MUSCLE CONSTRUCTS HAVING FUNCTIONAL TISSUE INTERFACES

(75) Inventors: Lisa M. Larkin, Ann Arbor, MI (US); Ellen M. Arruda, Ann Arbor, MI (US); Sarah Calve, Chicago, IL (US); Tatiana Y. Kostriminova, Schererville, IN (US)

(73) Assignee: The Regents of the University of Michigan, Ann Arbor, MI (US)

( * ) Notice: Subject to any disclaimer, the term of this patent is extended or adjusted under 35 U.S.C. 154(b) by 944 days.

(21) Appl. No.: 12/025,147

(22) Filed: Feb. 4, 2008

(65) Prior Publication Data

US 2008/0193910 A1    Aug. 14, 2008

Related U.S. Application Data

(60) Provisional application No. 60/899,178, filed on Feb. 2, 2007.

(51) Int. Cl.
*C12N 5/07* (2010.01)
(52) U.S. Cl. .................. 435/325; 435/373; 435/378
(58) Field of Classification Search .................. 435/101, 435/325, 373, 378
See application file for complete search history.

(56) References Cited

U.S. PATENT DOCUMENTS

| | | | |
|---|---|---|---|
| 4,605,623 A | 8/1986 | Malette | |
| 4,940,853 A | 7/1990 | Vandenburgh | |
| 5,153,136 A | 10/1992 | Vandenburgh | |
| 5,443,950 A | 8/1995 | Naughton | |
| 5,618,718 A | 4/1997 | Auger | |
| 5,756,350 A | 5/1998 | Lee | |
| 6,114,164 A | 9/2000 | Dennis et al. | |
| 6,207,451 B1 | 3/2001 | Dennis | |
| 6,303,286 B1 | 10/2001 | Dennis | |
| 6,448,076 B2 | 9/2002 | Dennis | |
| 6,777,234 B1 * | 8/2004 | Dennis et al. | 435/395 |
| 2004/0132184 A1 * | 7/2004 | Dennis et al. | 435/366 |

OTHER PUBLICATIONS

Erin L. Baker, Robert C. Dennis, and Lisa M. Larkin, Glucose Transporter Content and Glucose Uptake in Skeletal Muscle Constructs Engineered in Vitro, In Vitro Cell. Dev. Biol.—Animal 39:434-439, Nov.-Dec. 2003.
Robert G. Dennis, Paul E. Kosnik II, Mark E. Gilbert, and John A. Faulkner, Excitability and contractility of skeletal muscle engineered from primary cultures and cell lines, American Journal of Physiology—Cell Physiology, 280: C288-C295, 2001.
Robert C. Dennis and Paul E. Kosnik, II, Excitability and Isometric Contractile Properties of Mammalian Skeletal Muscle Constructs Engineered in Vitro, In Vitro Cell Dev. Biol.—Animal 36:327-335; May 2000.
A. Irintchev, J.D. Rosenblatt, M. J. Cullen, M. Zweyer and A. Wernig, Ectopic skeletal muscles derived from myoblasts implanted under the skin, Journal of Cell Science 111, 3287-3297, Oct. 28, 1998.
Paul E. Kosnik, John A. Faulkner, and Robert G. Dennis, Functional Development of Engineered Skeletal Muscle from Adult and Neonatal Rats, Tissue Engineering, vol. 7, No. 5, 2001.
Lisa M. Larkin, Jack H. Van Der Meulen, Robert C. Dennis, and Jeffrey B. Kennedy, Functional Evaluation of Nerve-Skeletal Muscle Constructs Engineered in Vitro, in Vitro Cell Dev. Biol.—Animal 42:75-82, Mar. and Apr. 2006.
Lisa M. Larkin, Sarah Calve, Tatiana Y. Kostrominova, and Ellen M. Arruda, Structure and Functional Evaluation of Tendon—Skeletal Muscle Constructs Engineered in Vitro, Tissue Engineering, vol. 12, No. 11, 2006.
Sarah Calve, Robert G. Dennis, Paul E. Kosnik II, Keith Barr, Karl Grosh, and Ellen M. Arruda, Engineering of Functional Tendon, Tissue Engineering, vol. 10, No. 5/6, 2004.
Yen-Chih Huang, Robert G. Dennis, Lisa Larkin, and Keith Barr, Rapid formation of functional muscle in vitro using fibrin gels, J Appl Physiol 98: 706-713, Oct. 8, 2004.

* cited by examiner

*Primary Examiner* — Ruth Davis
(74) *Attorney, Agent, or Firm* — Brooks Kushman P.C.

(57) ABSTRACT

A system and method for forming a skeletal muscle construct include primary muscle cells provided on a substrate without disposing the cells within an exogenous scaffold, the cells cultured in vitro such that the cells form a confluent monolayer; at least two anchors secured to the monolayer in spaced relationship; and at least one secondary tissue, such as neural or tendon tissue, provided in contact with the monolayer such that the monolayer detaches from the substrate and self-organizes to at least partially surround the at least one secondary tissue, thereby forming a three-dimensional skeletal muscle construct having a functional interface with the secondary tissue.

18 Claims, 24 Drawing Sheets

SYSTEM AND METHOD FOR FORMING SKELETAL MUSCLE CONSTRUCTS HAVING FUNCTIONAL TISSUE INTERFACES

CROSS-REFERENCE TO RELATED APPLICATIONS

This application claims the benefit of U.S. provisional application Ser. No. 60/899,178 filed Feb. 2, 2007, which is incorporated by reference herein.

STATEMENT REGARDING FEDERALLY SPONSORED RESEARCH OR DEVELOPMENT

The invention was made with government support under grant no. FA9550-05-1-0015 awarded by the Air Force Office of Scientific Research, grant no. CMS9988693 awarded by the National Science Foundation, and grant nos. R21 AR054359-01 and R01 AR054778-01 awarded by the National Institutes of Health; National Institute Of Arthritis And Musculoskeletal And Skin Diseases. The government has certain rights in the invention.

BACKGROUND OF THE INVENTION

1. Field of the Invention

This invention relates to a system and method for forming skeletal muscle constructs having functional tissue interfaces, such as neuromuscular and myotendinous junctions.

2. Background Art

End-stage organ failure or tissue loss is one of the most devastating and costly problems in medicine. Over 8 million surgical procedures are estimated to be performed each year incurring a health care cost of more than $400 billion annually. Organ and tissue replacement is limited by donor availability and immuno-rejection. Tissue engineering strives to develop biological substitutes that restore, maintain, or improve tissue function. There has been a great deal of activity in the area of in vitro muscle tissue engineering, however, muscle has not been successfully engineered to be functionally or phenotypically equivalent to adult skeletal muscle. Functional data for muscle refers to the active generation of force, work, and power, typically elicited by electrical stimulation. These measures are important in distinguishing muscles of different phenotypes. Developmental muscles are characterized by low excitability and specific force. In adult skeletal muscle, there are two predominant fiber types, slow and fast. Slow muscle has longer contraction and relaxation dynamics than fast muscle and reaches maximal force at a lower frequency of stimulation.

Myosin is the predominant protein in muscle, comprising around 25% of the total protein pool. Myosin is central to muscle function because it is the molecular motor that converts free energy released by the hydrolysis of ATP into mechanical work. Myosin heavy chain (MHC) isoform is the primary determinant of maximum shortening velocity, ATPase activity, maximum power output, and the rate of tension redevelopment. The expression of MHC genes is highly plastic, allowing skeletal muscles to adapt to changing functional needs during development and maturation, exercise training, and repair. A variety of factors, including developmental stage, innervation and the associated neuronal firing patterns, hormonal factors, and mechanical activity/inactivity have been shown to play important regulatory roles in the expression of MHC. During development and maturation, fibers initially express the embryonic MHC isoform, followed by neonatal, and then adult fast or slow isoforms. Chronic low frequency electrical stimulation increases the expression of the adult slow MHC. These data suggest that innervation increases the expression of adult MHC and that loading results in a shift from fast to slow MHC. In fact, it is nearly impossible to change the hormonal environment, innervation, or loading of a muscle in vivo without changing the MHC isoform expression.

In vivo, as the nervous system develops and innervation increases, fetal muscles shift towards the adult phenotype. Just as motor neurons control the expression of MHC in adult muscle, the motor neurons also exert this control during development of muscle cells. The control over fiber type expression is by two distinct mechanisms. The first is a local mechanism involving the release of neural regulatory factors at the level of the neuromuscular junction (NMJ) and the second mechanism is mediated by the activation pattern generated by the nerve. Acetylcholine receptors are among the first proteins expressed during myogenesis. Prior to innervation, acetylcholine receptors are randomly dispersed along the surface of the developing myoblast. During the formation of an NMJ, the chemotrophic, electrical, and mechanical signals between the nerve and muscle induce the aggregation of nicotinic acetylcholine receptors in the plasma membrane of the developing muscle fiber. The maintenance of the NMJ depends on continual cross-talk between the nerve and muscle at the site of nerve-muscle contact.

Tendons are highly organized connective tissues that transmit forces between muscle and bone. They are resilient during the development of tension but flexible enough to conform to their mechanically demanding environment. The mechanical integrity of tendon tissue can be attributed to the parallel fibrils of collagen. In the resting state, the collagen fibrils take on a wavy conformation, defined as the crimp. As a tendon is stretched, the crimped collagen fibrils begin to straighten out, and as a result, the tendon becomes stiffer with increasing application of mechanical strain.

Because of its relatively avascular nature, tendon is a prime candidate for engineered tissue replacement. Previous attempts have been made to create biologically based tendons in vitro, but these have met with limited success because of the difficulty in creating a construct that is both mechanically and biologically compatible with the in vivo environment. Native tendons possess an extracellular matrix (ECM) composed of many proteins, glycosaminoglycans, and proteoglycans that control the assembly of the load-bearing collagen fibril and contribute to the formation of the tissue hierarchy. Fibroblasts rely on cell-matrix signaling pathways during development to properly assemble the fibrils and maintain form and function after maturation.

The myotendinous junction (MTJ) is the structure that transmits force generated by a muscle contraction to the ECM of the muscle and onto the tendon. The morphology of the MTJ is characterized by folding of the sarcolemma into finger like projections at the interface between muscle and tendon at sites of myocyte termination. The projections result in approximately a ten-fold increase in the area of muscle-tendon contact over the cross-sectional area of the muscle fiber and ensure that the stresses experienced by the MTJ are shear stresses thus decreasing the contractile stress applied directly to the sarcolemmal junction. Therefore, the transmission of force between muscle and tendon is rarely associated with a severance at the interface between muscle and tendon, but rather occurs in the body of the muscle, just proximal to the MTJ.

Mechanical transduction of force across the MTJ activates cell signaling pathways that instruct the cells located at the interface to secrete and deposit proteins to form a specialized ECM at the MTJ. The increased expression of several ECM proteins of muscle and tendon, including focal adhesion kinase, paxillin, integrin linked kinase, mitogen-activated protein kinase, and talin, has been shown to occur in response to increased mechanical loading of the MTJ. These proteins provide a conduit by which forces can be transmitted from muscle to tendon. Lack of the expression of these proteins at the MTJ has been shown to lead to structural damage of the interface during contraction.

DETAILED DESCRIPTION OF THE INVENTION

Figure 1A:
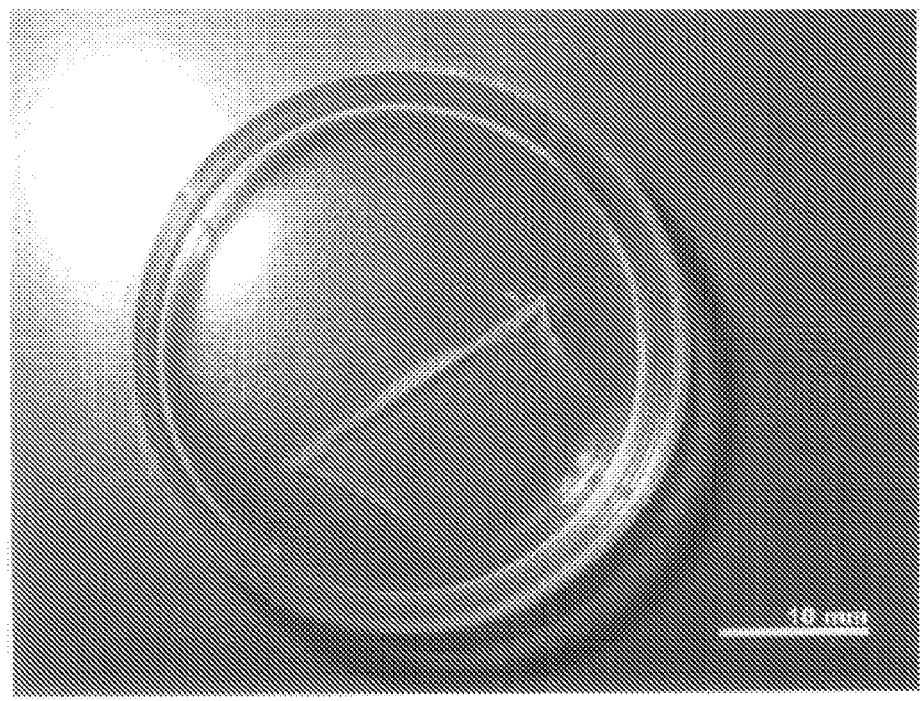
FIGS. 1A-C are photographs of a muscle cell monolayer with two spinal cord explants from E-15 fetal rats pinned thereto (A), E-15 neural tissue integrating with muscle monolayer (B), neural tissue forming extensions projecting from the nerve-muscle construct according to the present invention.

As required, detailed embodiments of the present invention are disclosed herein; however, it is to be understood that the disclosed embodiments are merely exemplary of the invention that may be embodied in various and alternative forms. The figures are not necessarily to scale, some features may be exaggerated or minimized to show details of particular components. Therefore, specific structural and functional details disclosed herein are not to be interpreted as limiting, but merely as a representative basis for teaching one skilled in the art to variously employ the present invention.

The present invention includes a contractile, self-organizing, three-dimensional skeletal muscle tissue construct having a functioning tissue interface, such as a neuromuscular junction (NMJ) or a myotendinous junction (MTJ), and a system and method of engineering the construct by a co-culture of myogenic cells with a secondary tissue (e.g., neural or tendon tissue) without the use of exogenous scaffolding. By way of example, the skeletal muscle tissue constructs and systems and methods for their production according to the present invention are described with reference to the use of tissue harvested from rats. However, it is fully contemplated that tissue from any mammal, including human beings, could be similarly utilized according to the method described herein. The construct, system and method of the present invention are not intended to be limited to one particular cell origin or age, construct shape, time frame, component concentration, or culture condition. One skilled in the art can readily appreciate that various modifications can be made to the construct, system and method described herein without departing from the scope of the invention disclosed.

Unless otherwise indicated, all solutions and media described herein may be prepared and stored at 4 C before, and then warmed to 37 C in a heated water bath immediately before use. It is understood that all reagent measurements, materials, submersion times, and other values described herein are approximate, and can be reasonably varied without affecting the method and resulting constructs. Furthermore, the approximate volumes of reagents within solutions described herein may be altered to provide a solution with reagents having similar volume ratios.

A reproducible technique for engineering self-organized, scaffold-free 3-D skeletal muscle tissue is described in commonly assigned U.S. Pat. No. 6,207,451, incorporated by reference herein. The 3-D muscle tissue produced in this manner, termed a "myooid," contracts spontaneously producing ~25 µN of force. When stimulated electrically, myooids produce a peak twitch force of ~320 µN and a tetanic force of ~575 µN. Myooids also display many important functional similarities with skeletal muscle in vivo, including positive force-frequency and length-tension relationships. When the maximal twitch and tetanic forces are normalized to cross-sectional area, myooids produce a specific force of 5-20 $kN/m^2$. While this represents the highest published specific force generated by an engineered 3-D skeletal muscle, it is only 2-8% of typical adult values or 5-30% of neonatal muscles. However, this specific force and contractility data suggest that engineered muscle constructs contain embryonic and neonatal MHC ready for the proper cues to develop.

The system and method according to the present invention provide a self-organizing, 3-D nerve-muscle construct using a co-culture of a confluent monolayer of myotubes and neural tissue, such as in the form of embryonic day 15 (E-15) rat spinal cord with dorsal root ganglia attached. The introduction of neural tissue to developing engineered muscle constructs according to the present invention leads to functional motor innervation of the muscle constructs and a shift toward the adult phenotype, and the nerve-muscle constructs exhibit an increase in force production and adult MHC expression as described further below.

Tissue engineering according to the present invention is carried out using muscle tissue from female Fischer 344 pregnant rats obtained from the Charles River Laboratories, Inc. (Wilmington, Mass.). At E15 gestation day, surgical procedures are performed to remove both soleus muscles and tail tendon from the pregnant mom, and spinal cord explants are obtained from the E15 fetuses. All surgical procedures are performed in an aseptic environment with animals in a deep plane of anesthesia induced by i.p. injections of sodium pentobarbital (65 mg/kg).

The chemical acellularization method according to the present invention has been described in the context of acellularizing skeletal muscle tissue in commonly assigned U.S. Pat. No. 6,207,451, tendon tissue in commonly assigned U.S. Ser. No. 10/602,789, and cardiac muscle tissue in U.S. Patent Publication No. 2004/0132184, each of which is incorporated by reference herein.

Media utilized according to the present invention is as follows. Growth medium (GM) utilized may include 400 ml of HAM F-12 Nutrient Mixture (Gibco BRL Cat #11765-054), 100 ml fetal bovine serum (Gibco BRL Cat #10437-028), and 5 ml A9909 (Sigma A9909). Differentiation medium (DM) may include 465 ml Dulbecco modified Eagle medium (DMEM; Gibco BRL Cat #11995-065), 35 ml 100% horse serum albumin (Gibco BRL Cat #16050-122), and 5 ml A9909. The tissue is dissociated in a dispase and collagenase solution (D&C) that may be prepared in the amount of 20 ml per four soleus muscles and including 8 units Dispase (Sigma Cat #P-3417; 0.4 units/mg) and 200 units of type 4 collagenase (Gibco BRL Cat# 17104-019; 239 units/mg) per ml DMEM. Transport medium (TM) may be prepared in the amount of 5 ml per muscle dissected at the concentration of 2% A9909 in DPBS. Preincubation medium (PIM) may be prepared in the amount of 3 ml per plate and including 2.5 ml of 0.05% sodium azide ($NaN_3$; Sigma Cat #S-8032) in DPBS solution, 22.5 ml DMA, and 0.25 ml A9909 per muscle dissected.

Myooids may be engineered in individual tissue culture plates (e.g., 35 mm) which serve as a substrate for construct formation as described in U.S. Pat. No. 6,207,451. Each 35-mm plate may be coated with 1.5 ml of SYLGARD® (Dow Corning Corp., Midland, Mich.; type 184 silicon elastomer) and allowed to cure for ~3 wk before use. Approximately one week before use, SYLGARD®-coated plates may be coated with laminin at 1.0 $mg/cm^2$ per plate (10 mg of natural mouse laminin [Gibco BRL Cat #23017-015] and 3 ml of Dulbecco phosphate-buffered saline [DPBS] pH 7.2 [Gibco BRL Cat #14190-144] per plate) and left to dry for ~48 h. Salt crystals may be dissolved and removed by rinsing the plates with 3 ml DPBS. The plates may then be filled with 2 ml of previously described GM and decontaminated with UV light (e.g., wavelength 253.7 nm) for ~90 min and placed in a 37 C 5% $CO_2$ incubator for ~1 wk before plating muscle cells.

For the preparation of muscle and the isolation of satellite cells, both soleus muscles may be surgically removed under aseptic conditions, weighed, sterilized in 70% ETOH, and incubated for ~5 min in TM. The soleus muscle may be sliced longitudinally into a plurality of strips (e.g., three). Next, 35-mm SYLGARD®-treated plates may be sterilized in 70% ETOH, and muscle slices pinned to length, for example, two muscle strips per plate. Then, 3 ml PIM may be added to each plate, and the plates UV-treated for 90 min. The plates are then placed in a 37 C 5% $CO_2$ incubator for ~50 h. Following the incubation period, muscle slices may be inspected for contamination, and any infected plates discarded. The remaining muscle strips may then be removed from the plates and incubated in D&C (two soleus muscles per 20 ml) in a 37 C shaking water bath for ~4 h. The dissociation may be aided by occasionally shaking each vial slightly by hand. Once the muscle is fully digested, the dissociated cells may be filtered through a 100-micron filter and centrifuged at 700 g for 10 min at 25 C. Finally, the supernatant is aspirated from the vials, and the pellet may be re-suspended in GM to obtain a concentration of 10 mg of dissociated muscle per 2 ml GM.

Figure 1B:
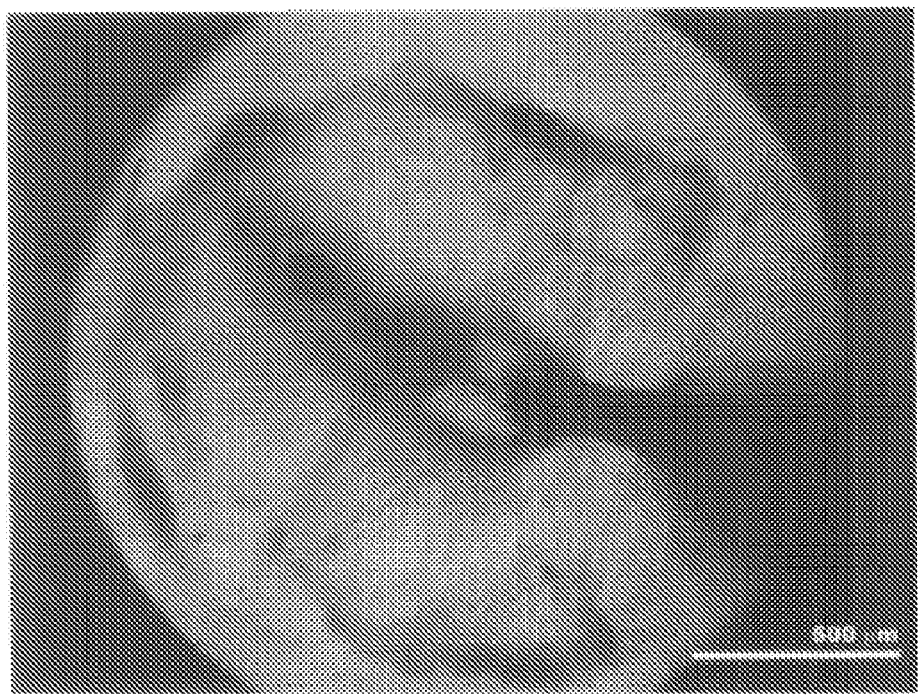
Figure 1C:
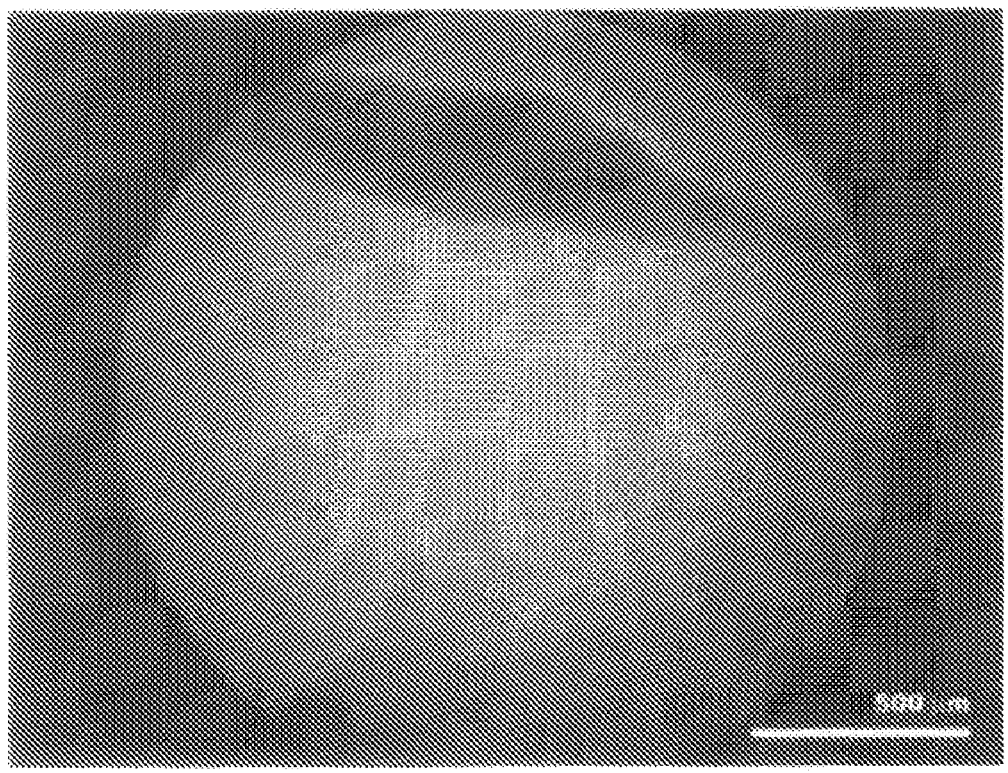

After storage in an incubator for ~1 wk, the GM is aspirated from the previously-prepared plates. Two milliliters of the primary muscle cell suspension may be plated in each culture dish and placed in a 37 C 5% $CO_2$ incubator for ~5 d without disposing the cells within exogenous scaffolding. According to one aspect of the present invention, culture plates should not be disturbed for at least ~72 h to allow cell adherence to the plates. After 5 d, the cells are fed with GM every ~48 h until the cells became confluent (approximately 7 d). Once the cells achieve confluence, they may be fed with DM every 48 h until the myocytes fuse to form multinucleated myotubes that begin to contract spontaneously. Approximately two weeks after the initial plating of the primary muscle cells, neural tissue is placed in contact with the muscle cell monolayer. According to one aspect of the present invention, the neural tissue may include one or more spinal cord explants from E-15 fetal rats, which may have the tail still attached, which are secured to the muscle cell monolayer via pins in spaced relationship (e.g., ~12 mm apart), wherein the tail portion may be oriented toward the edge of the dish (FIG. 1). The at least two pins also serve as anchors for constraining the shape of the developing construct. Approximately 1 wk later, the monolayer detaches from the substrate and rolls up to at least partially surround the tail anchors and form a self-organized cylindrical nerve-muscle construct according to the present invention.

Sixteen to 18 d post construct formation, the nerve-muscle constructs were tested for contractile function. At the conclusion of functional tests, each specimen was snap frozen between dry ice and stored for subsequent analysis of MHC profile. Muscle constructs including primary muscle cells and adult rat tail tendon served as control for the nerve-muscle constructs.

Figure 2:
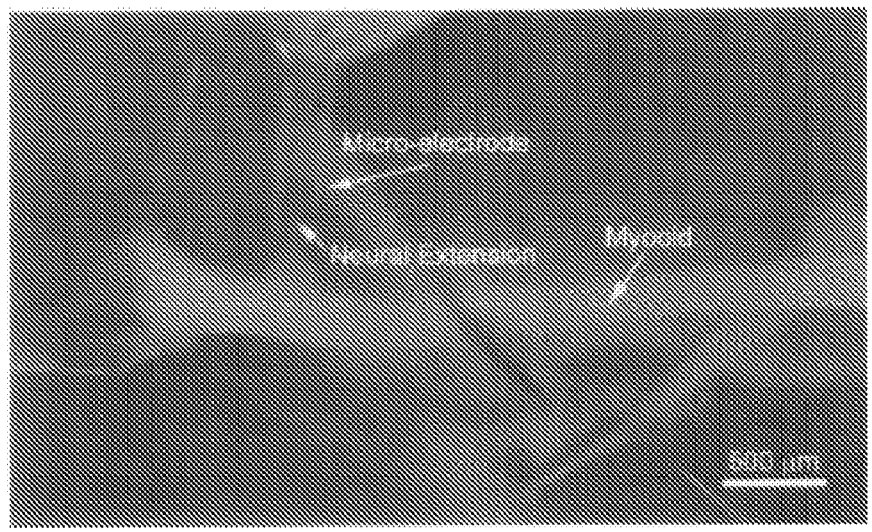
FIG. 2 is a photograph of a nerve-muscle construct according to the present invention with a neural extension.

The protocol for measuring contractility of engineered muscle constructs was as follows. The pin on one end of the construct was freed from the SYLGARD® and attached to a force transducer with canning wax. For field stimulation of the entire construct, platinum wire electrodes were positioned on either side of the construct. The temperature of the construct was maintained at ~37 C using a heated aluminum platform. The diameter of the construct was determined and used to calculate cross-sectional area, assuming a circular cross-section. Passive baseline force was measured as the average baseline passive force preceding the onset of stimulation. Twitches were elicited using a single 1.2-ms pulse at 2.5, 5, 10, and 20 V, whereas maximum tetanic force was determined using a 1-s train of 1.2-ms pulses at 10 V and 10, 20, 40, 60, and 80 Hz. Data files for each peak twitch force and peak tetanic force trace were recorded at 1000 samples/s and stored for subsequent analysis using LabVIEW data acquisition software. Peak tetanic force was normalized for cross-sectional area to determine maximum specific force. Following the direct field stimulation of the entire construct, a microelectrode was used to electrically stimulate the neural extensions projecting from the construct (FIG. 2) using the same stimulation parameters as described previously for the field stimulation.

Western analysis of MHC was conducted as previously described (Talmadge and Roy, *J. Appl. Physiol.* 75(5): 2337, 1993). Muscle-only and nerve-muscle constructs (n=5) were homogenized in phosphate buffer in a 1:100 (wt/vol) dilution. Twenty microliters of homogenate was used to determine proteins via Bradford protein assay (Biorad, Richmond, Calif.). Western analysis was performed by using a vertical SDS page gel electrophoresis in the presence of sodium dodecyl sulfate and aliquots of muscle membranes (2 mg protein per lane). Several internal control samples of adult rat soleus, rat E-15 fetal limb buds, and rat 3-d-old neonatal limb muscle were run on all gels, and duplicate samples from each myooid were separated on an 8% polyacrylamide-glycerol resolving gel and then eletrophoretically transferred onto Immobilon polyvinyldifluoride membrane (Millipore, Milford, Mass.). Immunoblotting was performed by using antibodies against rat MHC slow (Cat #-NCL-MHCs), MHC fast (Cat #-NCL-MHCf), MHC neonatal (Cat #-NCL-MHCn), and MHC developmental (Cat #-NCL-MHCd) obtained from (Novocastra Laboratories Ltd, Newcastle, United Kingdom), followed by chemiluminescent labeled IgG (Jackson Laboratories, Bar Harbor, Me.), and the chemiluminescent signal was monitored, digitized, and analyzed using autoradiography. Myooid signals were corrected for background and MHC signals were compared to the adult soleus, fetal, and neonatal muscle signals.

Values are presented as means ±SE. Statistical analysis was performed by using Jump In 5.1 (SAS Institute Inc., Cary, N.C.). A one-way analysis of variance was conducted to compare the differences between myooids and nerve-muscle constructs. Differences were considered significant at $p<0.05$.

Figure 3A:
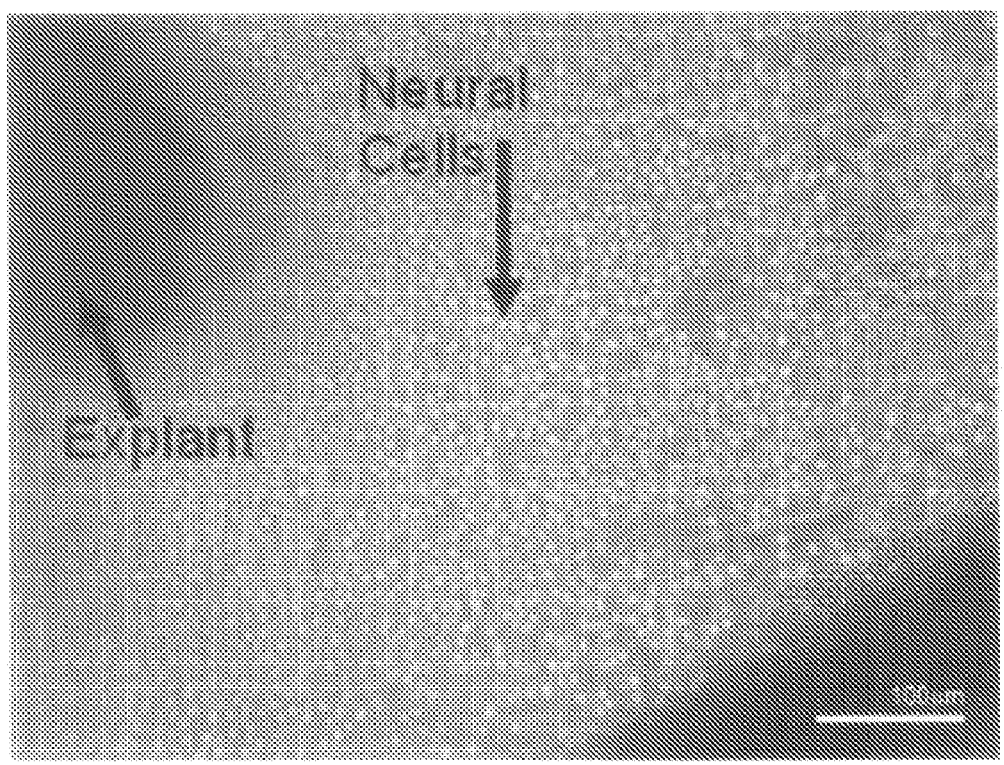
FIGS. 3A-B are light micrographs of E-15 fetal spinal cord explants following 3 d of co-culture with muscle cell monolayers depicting neural cells first migrating away from the site of the explant (A) and then aggregating to form larger neural extensions (B)
Figure 3B:
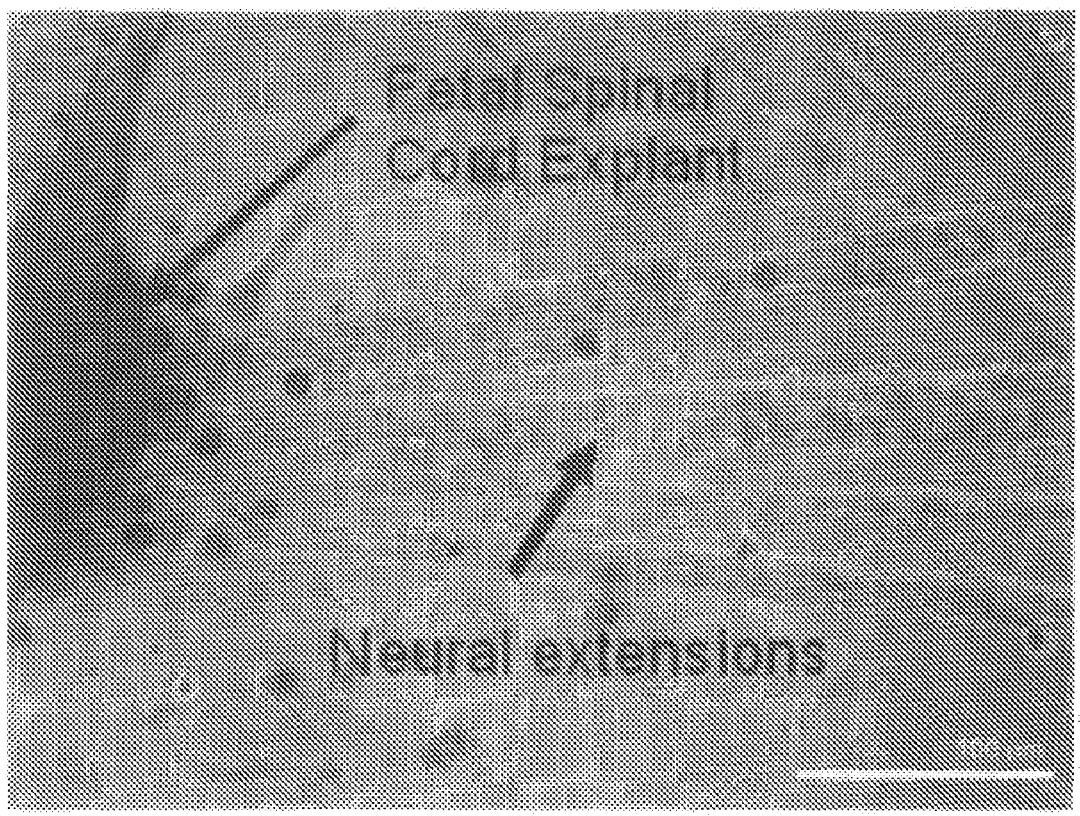
Figure 4A:
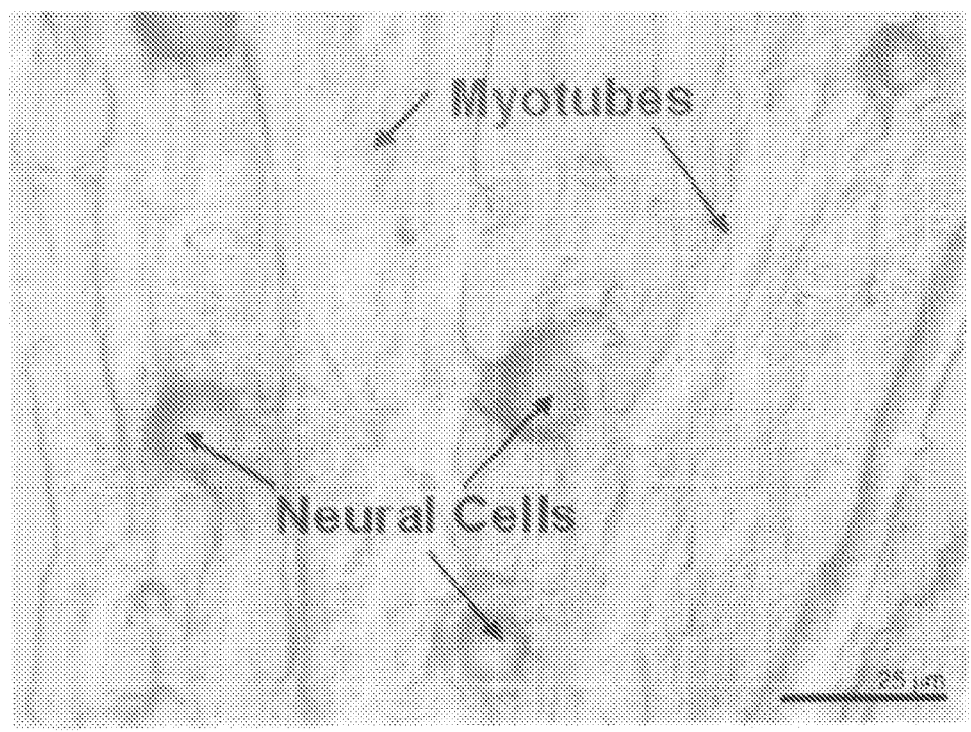
FIGS. 4A-B are (A) a light micrograph of myotubes and neural cells and (B) a fluorescent image of neural cells stained with CY3-labeled neurofilament following 1 wk of co-culture.
Figure 4B:
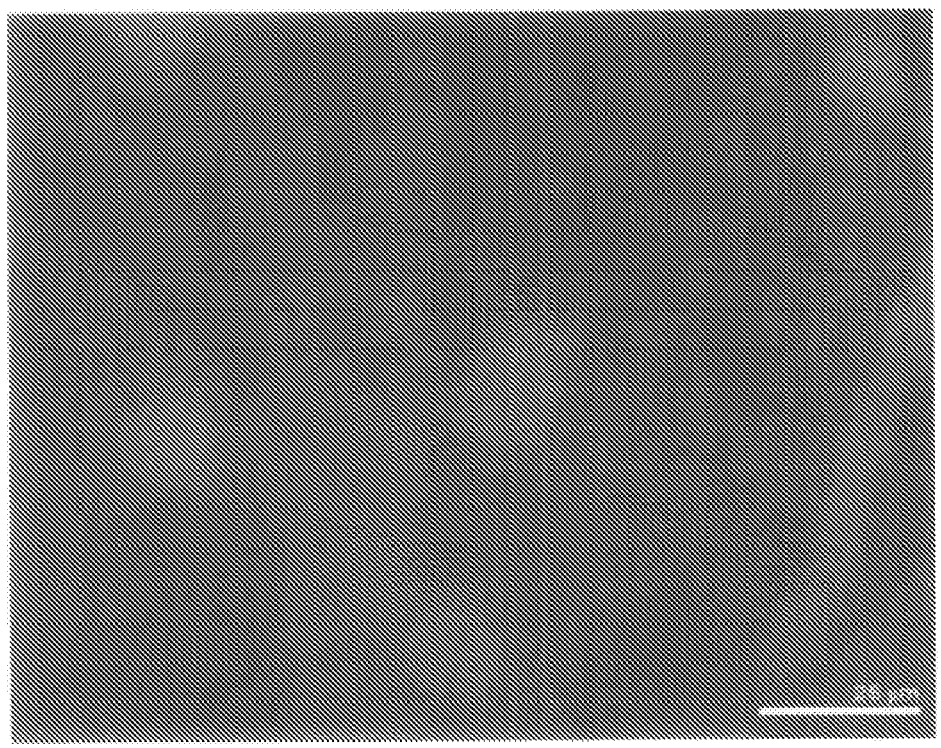
Figure 5:
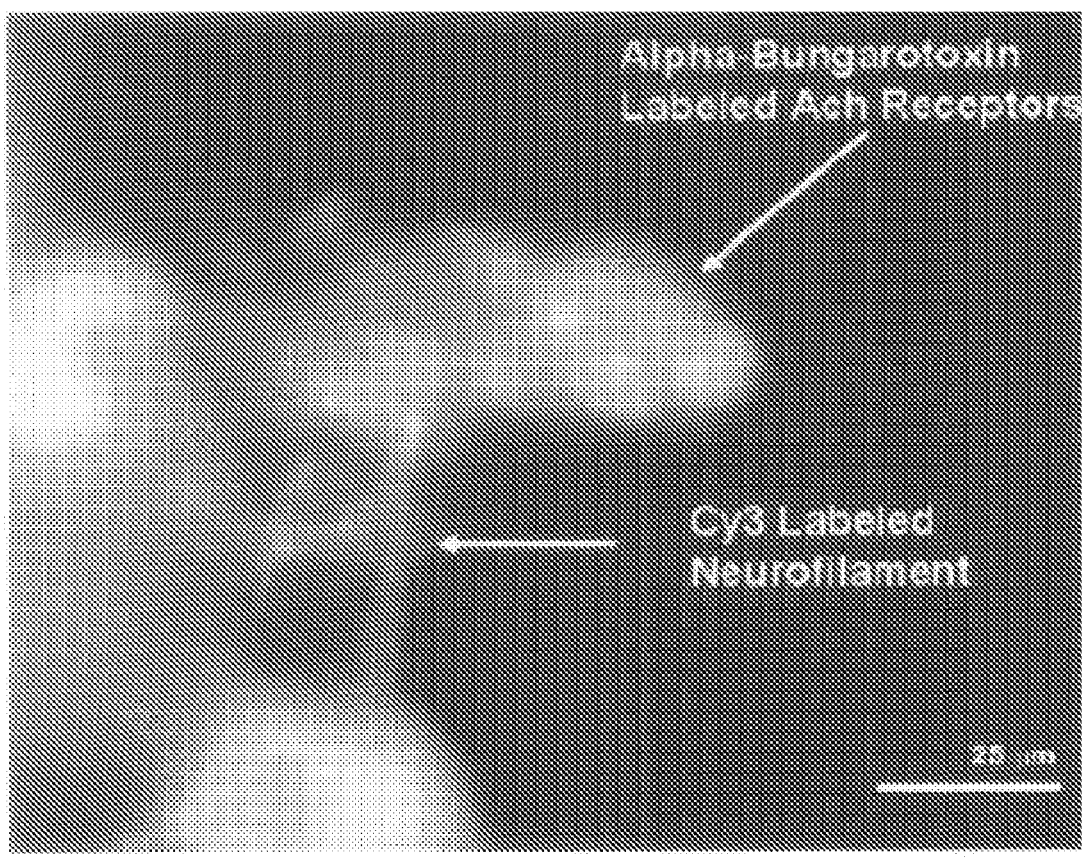
FIG. 5 is a fluorescent microscopy image of neuromuscular junctions formed between rat fetal spinal cord explants and a three-dimensional muscle construct according to the present invention, wherein immunohistochemistry indicates that the muscle constructs contain the Ach receptors necessary for innervation and that these receptors are clustered in a structure resembling a neuromuscular junction.

Approximately 1 wk after the introduction of the neural tissue explant, neuronal cells from the explants migrate away from the explant and move across the monolayers of myotubes (FIG. 3). Many of the neural cells fuse with the myotubes (FIG. 4), and others form neuromuscular-like junctions with clustering of acetylcholine (Ach) receptors surrounded by neurofilament-stained neural extensions (FIG. 5). The costaining of neuronal-derived tissues with neurofilament and Ach receptors with alpha-bungarotoxin allows for the identification of NMJs. During development, Ach receptors are dispersed randomly along the plasma membrane of myotubes. Introduction of the E-15 fetal rat spinal cord according to the present invention results in the clustering of the Ach receptors. In addition, neuronal clefts and projections form around and away from the cluster of Ach receptors. Morphologically, the introduction of the E-15 spinal cord results in what resembles architecturally an NMJ.

Figure 6A:
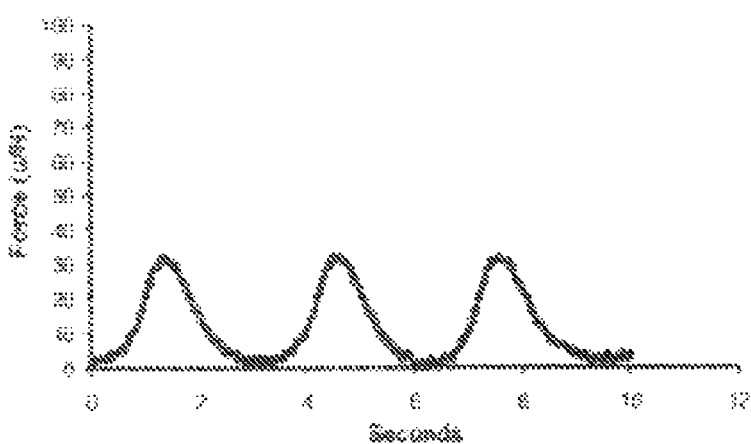
FIG. 6A-C are representative force traces for baseline, twitch, and tetanus, respectively, in response to field stimulation across the nerve-muscle constructs according to the present invention.
Figure 6B:
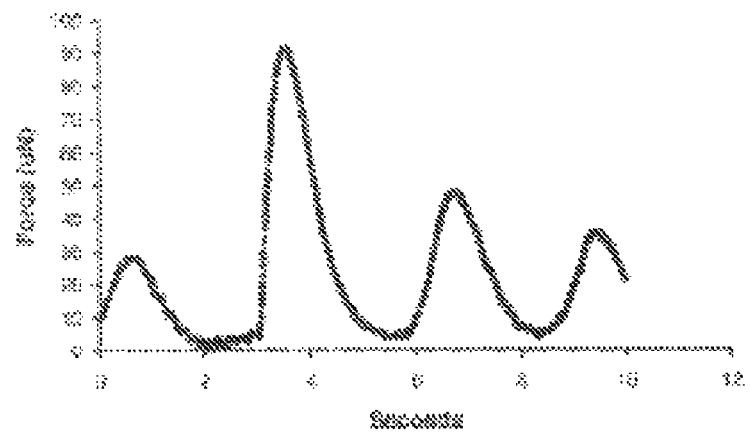
Figure 6C:
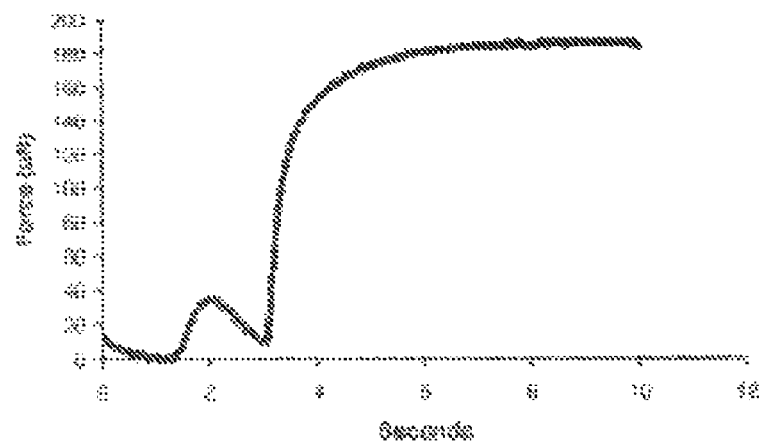

A representative tracing from a nerve-muscle construct according to the present invention is shown in FIG. 6. The nerve-muscle constructs show the same response to field stimulation as previously described for muscle-only constructs. The nerve-muscle constructs exhibit spontaneous baseline activity and can elicit both a twitch and a tetanus response to a field stimulation (FIG. 6). Following the field stimulation of the nerve-muscle construct, microelectrodes were used to electrically stimulate the neural extensions radiating from the construct. The maximum tetanus generated from the neural extension was approximately 25% of the total tension elicited with field stimulation, suggesting that the neural extension was recruiting approximately 25% of the myotubes in the construct during the contraction (FIG. 7).

Figure 7A:
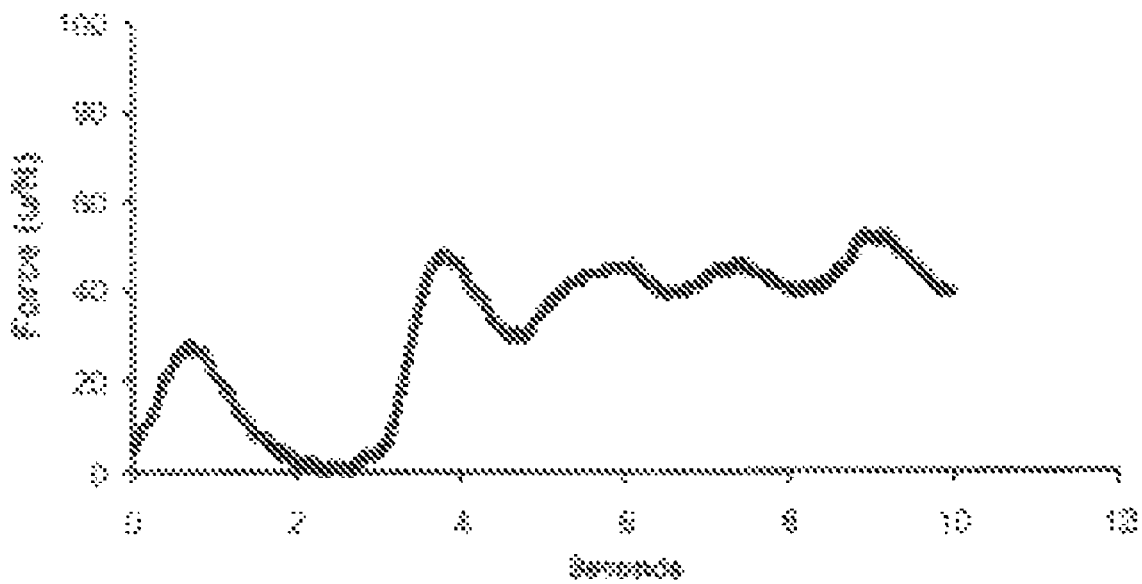
FIGS. 7A-B are representative tetanus recordings of nerve-muscle constructs according to the present invention during the direct stimulation of an attached neural extension before and following the severing of the neural extension, respectively.
Figure 7B:
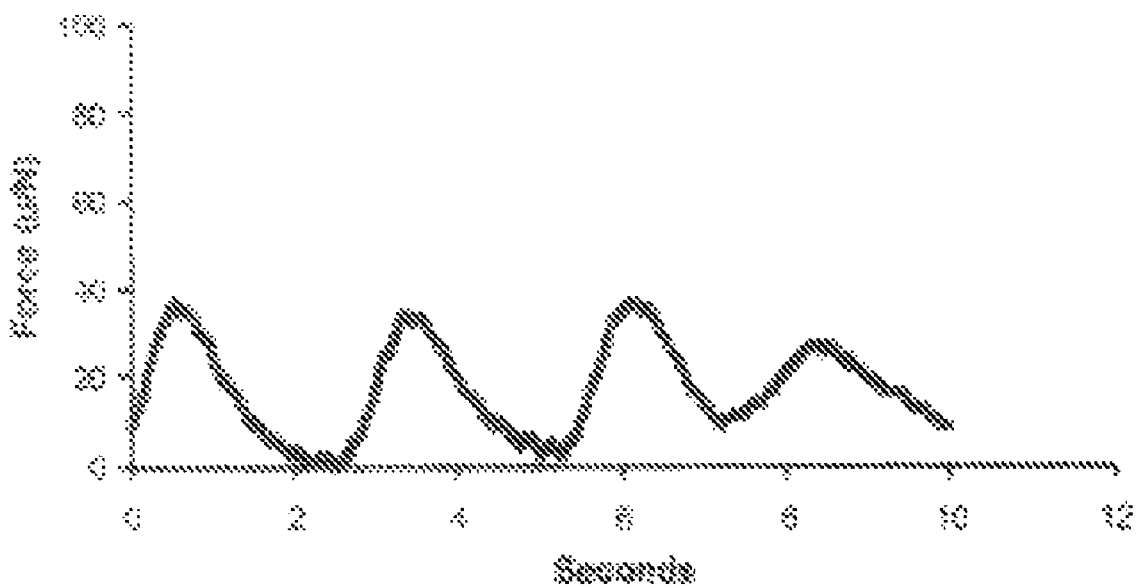
Figure 8A:
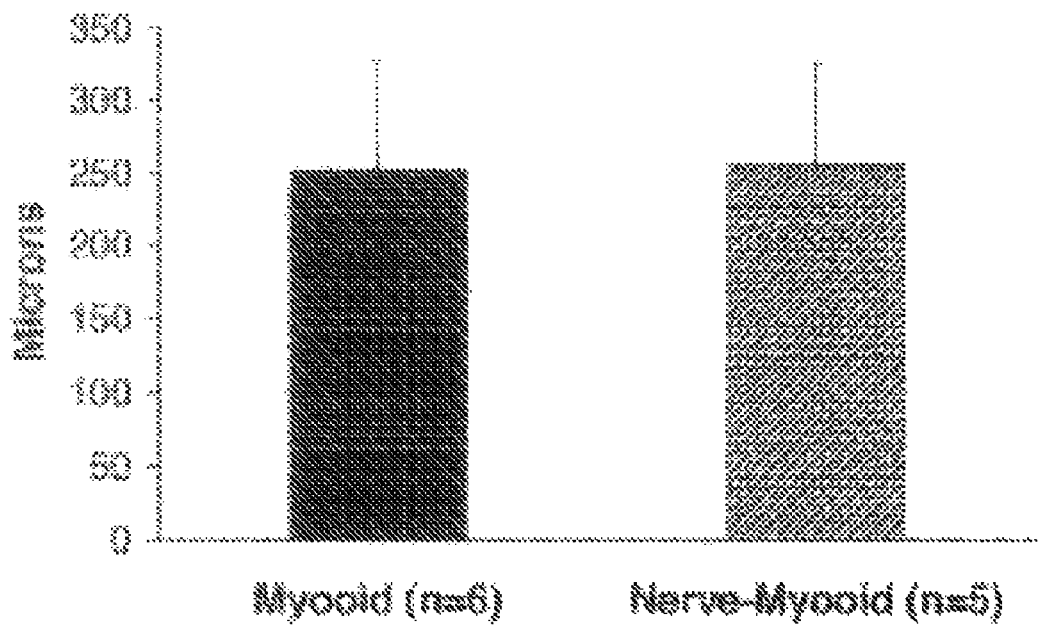
FIGS. 8A-C are graphs depicting the diameter, twitch, and tetanus, respectively, of muscle and nerve-muscle constructs, wherein values are means ±SE.
Figure 8B:
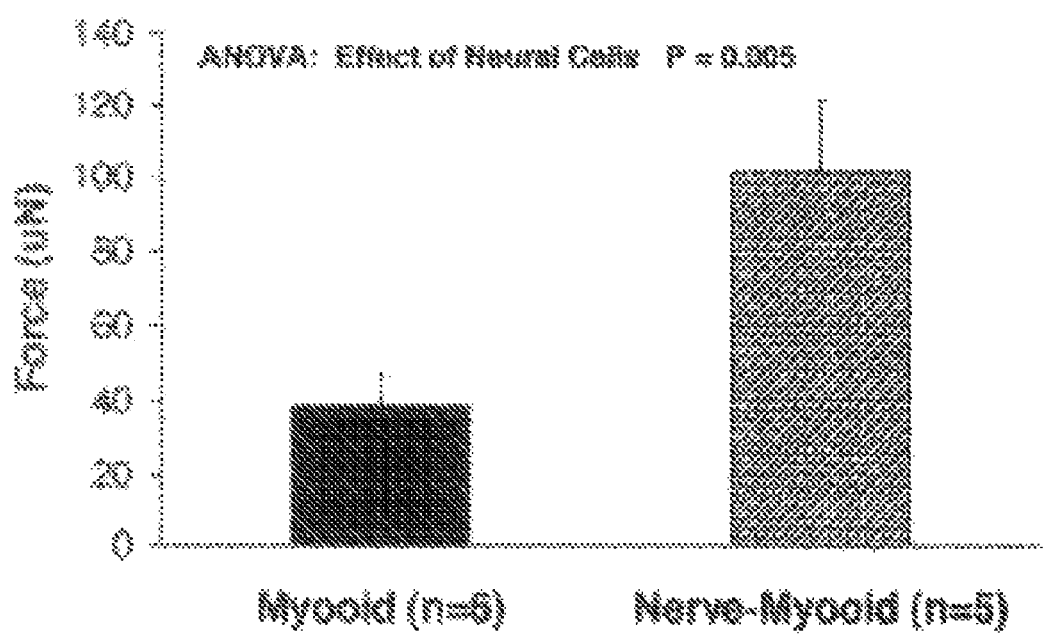
Figure 8C:
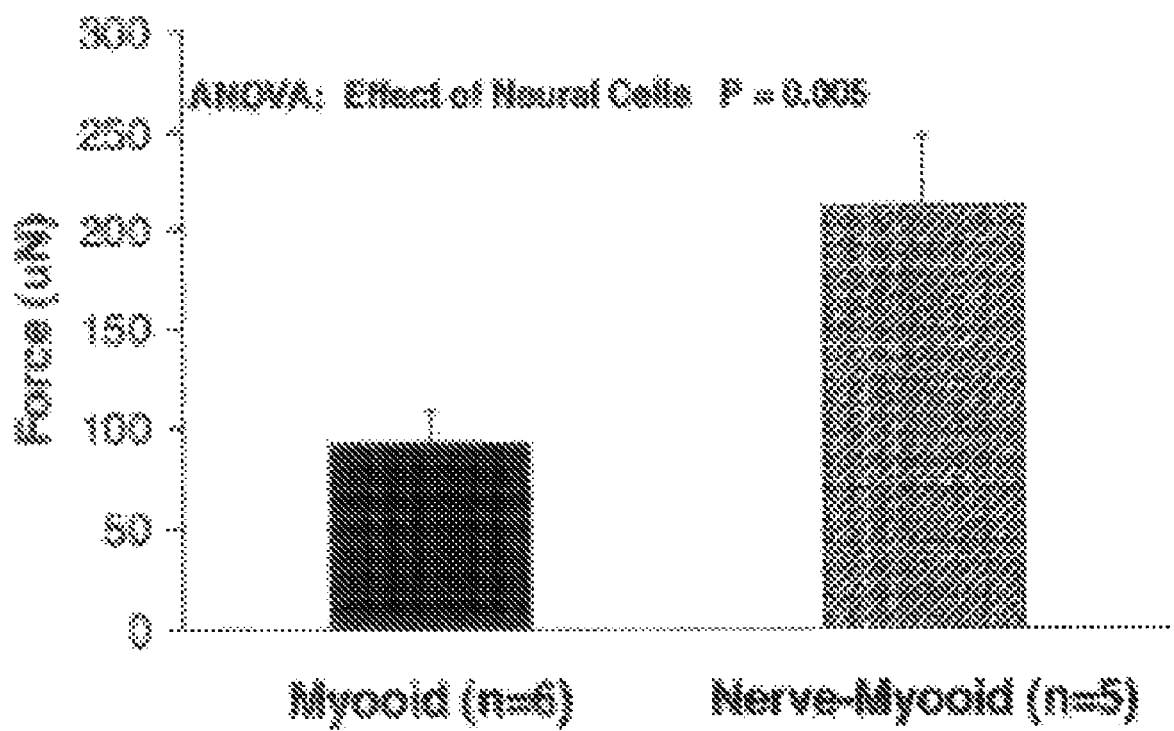

Following the severing of the extension without altering the position of the microelectrode, the nerve-muscle construct returned to spontaneous baseline contractile activity (FIG. 7). The nerve-muscle construct would no longer respond to stimulation of the nerve via the microelectrode, indicating that the stimulation via the microelectrode was not due to the proximity of the electrode to the construct but actually elicited the stimulation along the neural projection. The average diameters of the myooid and nerve-muscle constructs were not significantly different (FIG. 8). The average maximum twitch and tetanus generated by field stimulation was significantly greater in the nerve-muscle constructs according to the present invention versus the myooids ($P=0.005$ and $P=0.005$, respectively). The increase in both twitch and tetanus force elicited by field stimulation in the nerve-muscle versus the muscle-only constructs further suggests that the sarcomeres present in the nerve-muscle constructs are capable of producing more force compared to muscle-only constructs.

Figure 9A:
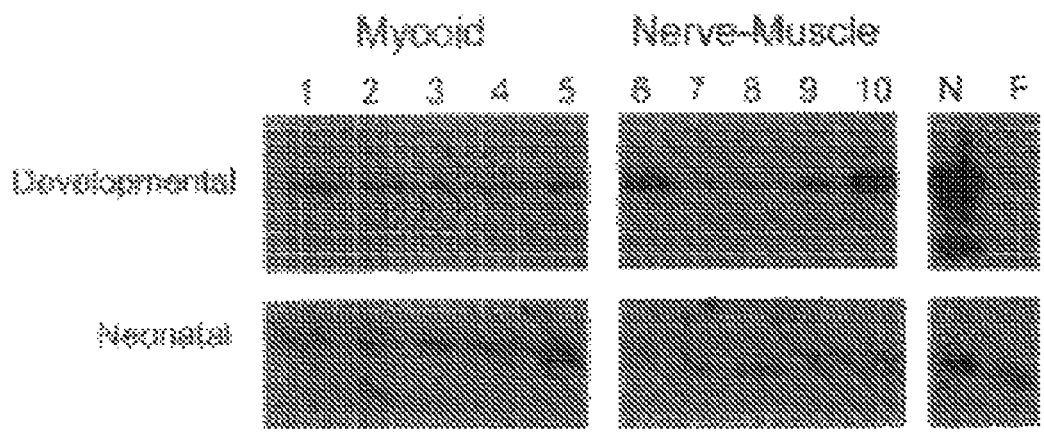
FIGS. 9A-C depict (A) Western blots of muscle (myooid) and nerve-muscle constructs according to the present invention probed for neonatal and developmental MHC proteins; and graphs of the average expression of developmental (B) and neonatal (C) MHC expressed as a percentage of the myooid expression, wherein values are means ±SE.
Figure 9B:
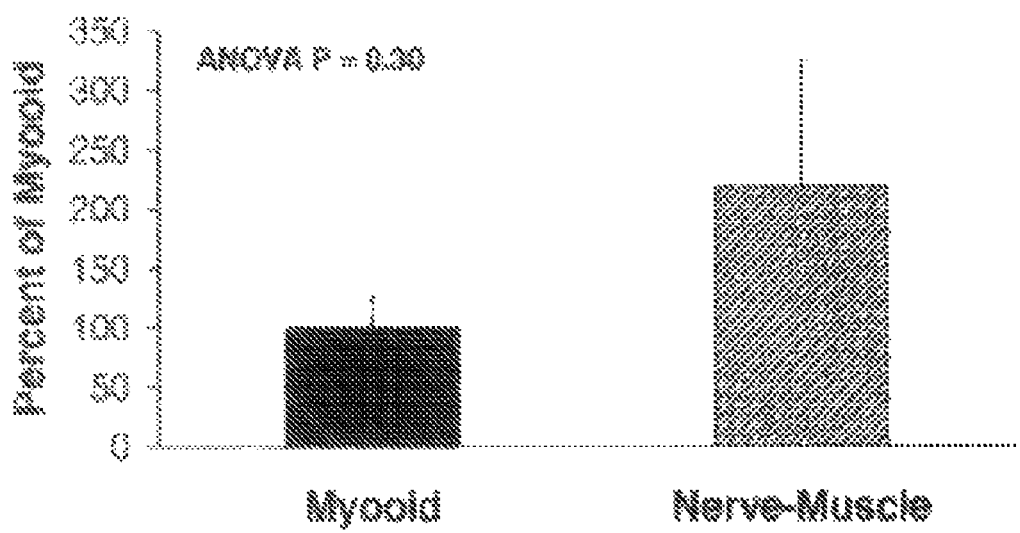
Figure 9C:
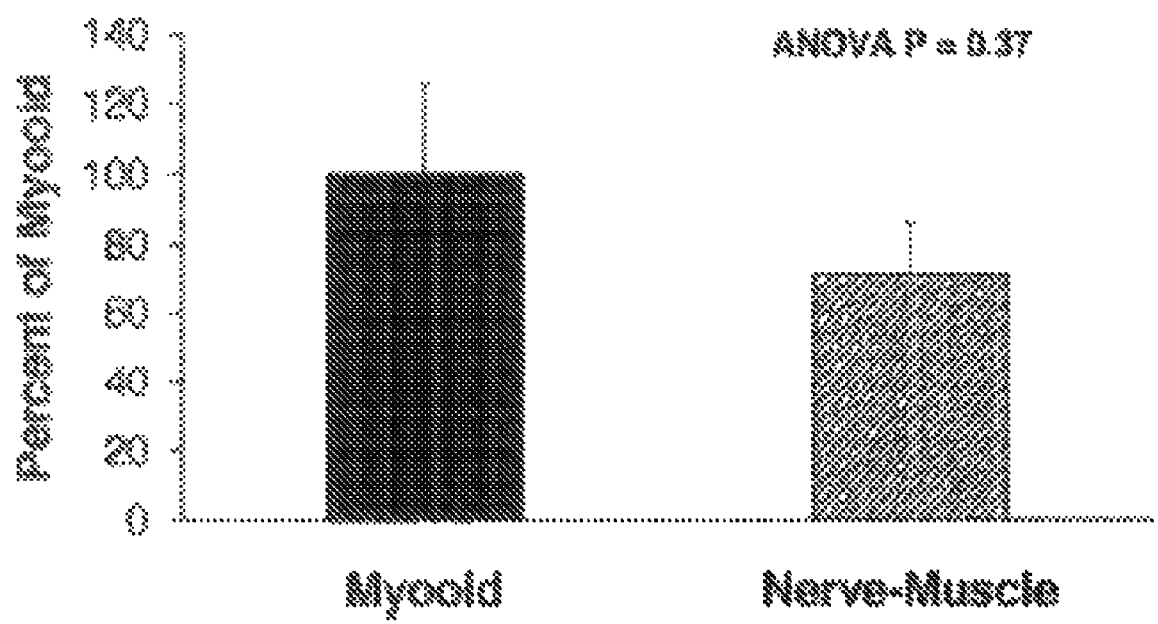
Figure 10A:
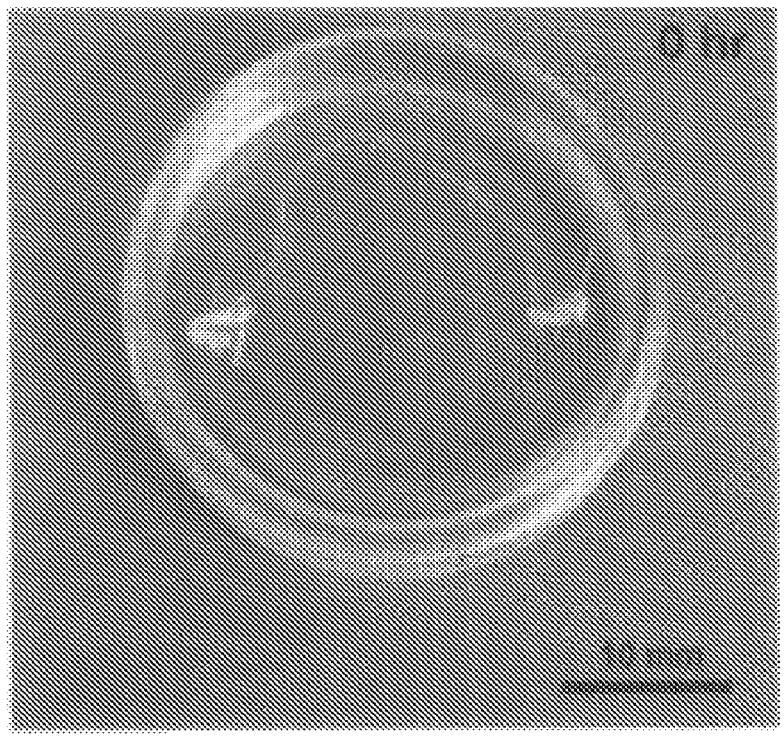
FIGS. 10A-D are photographs illustrating the delamination and construct formation of muscle-tendon constructs according to the present invention, progressing from the start of monolayer detachment (A), through 8 hr (B), 16 hr (C), and 24 hr (D) when three-dimensional construct formation is complete.
Figure 10B:
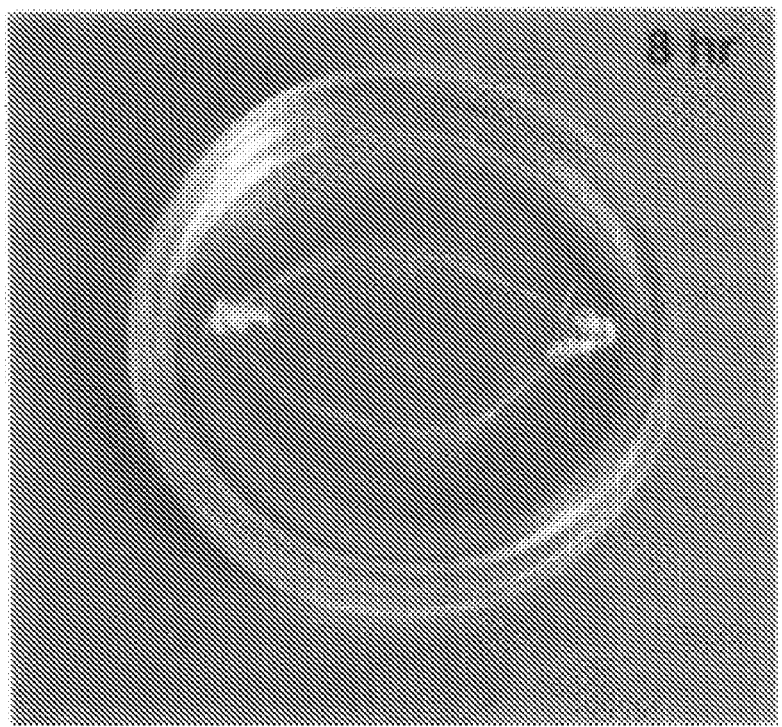
Figure 10C:
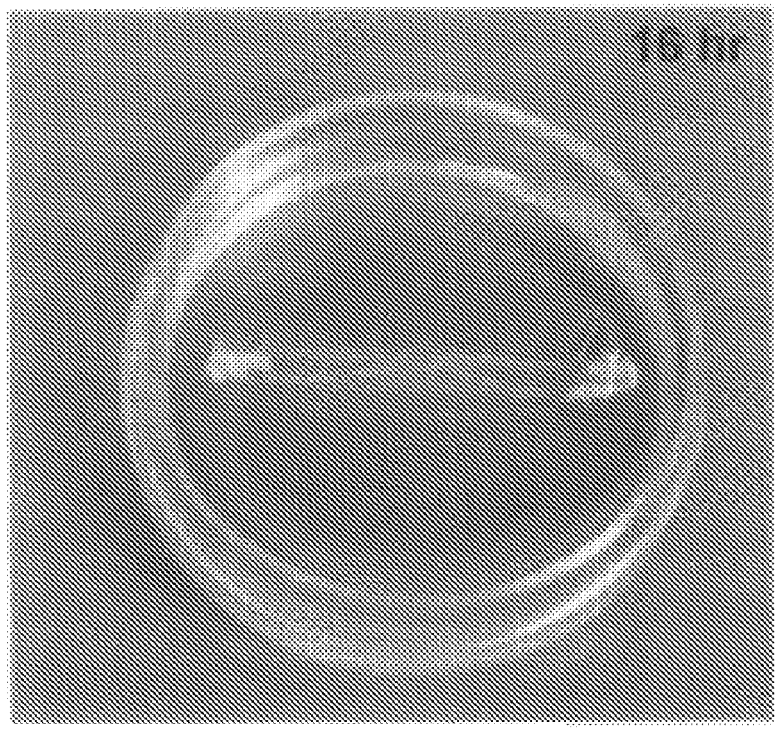
Figure 10D:
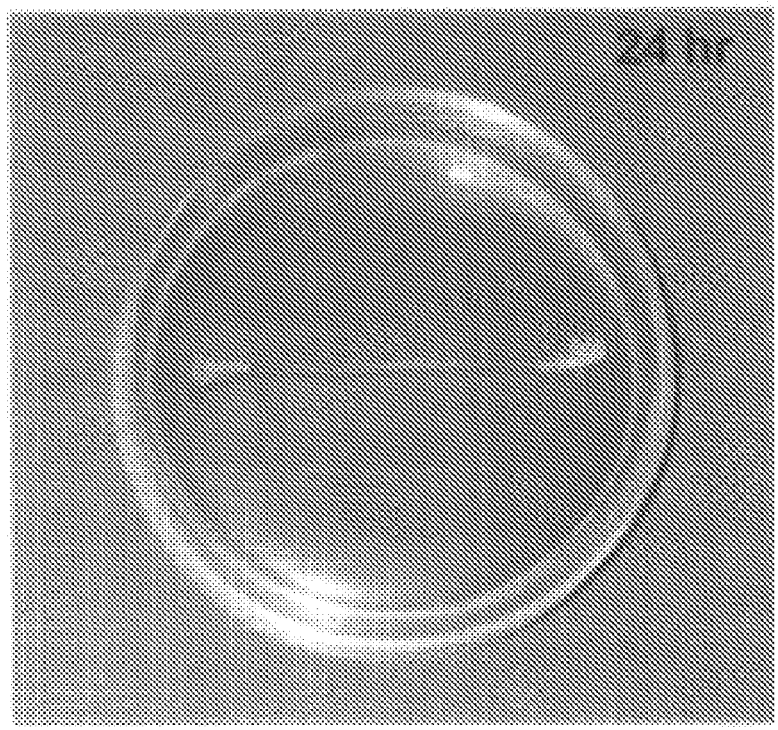

Western analysis of the MHC content in the nerve-muscle constructs according to the present invention versus myooid constructs is shown in FIG. 9. The sample from 3-d-old neonatal limb muscle showed the greatest expression of myosin per gram of protein than any other sample with a greater signal with the developmental antibody and gave a moderate signal with the neonatal antibody. The fetal E-15 limb bud sample only gave a signal with the neonatal antibody. These tests indicated that the expression of both developmental MHCs tended to be greater, while the neonatal MHCs tended to be less in the nerve-muscle constructs versus myooid constructs, suggesting that the myosin content per total gram of protein is greater in the nerve-muscle constructs, and that there was a greater content of neonatal versus fetal MHC isoform in the nerve-muscle constructs versus the muscle-only constructs.

Therefore, according to the present invention, three-dimensional nerve-muscle constructs may be constructed from co-cultures of myogenic cells with neural tissue explants. The nerve-muscle constructs include functional neural muscular junctions and neural muscular projections that respond to electrical stimulation by contraction. The introduction of the neural cells to a muscle construct according to the present invention results in nerve-muscle constructs with functional NMJs that generate more force per gram of tissue than muscle-only constructs. In addition, the system and method according to the present invention alter the MHC profile from that of a fetal to a more neonatal phenotype as indicated by the increase in the neonatal form of MHC in the nerve-muscle constructs compared to muscle-only constructs.

The functionality of the nerve-muscle constructs according to the present invention, that is, the ability to convey an action potential from the nerve across the junction to elicit a muscular contraction, was verified by stimulation with specially designed microelectrodes. Using field stimulation, which elicits an electrical stimulation along the entire length of the muscle construct, the same mechanical response was observed as previously described for muscle-only constructs. The nerve-muscle constructs exhibit spontaneous baseline activity and both a twitch and a tetanus response to field stimulation. The contractility of the nerve-muscle constructs according to the present invention is greater than that of muscle-only constructs. The cumulative signal from the MHC Western suggests that there is more muscle tissue per gram of total tissue in the nerve-muscle constructs than the muscle-only constructs. The diameters of the nerve-muscle versus muscle-only constructs were not different, and the addition of the neural tissue to the monolayer of muscle would suggest a decrease in muscle per diameter of the construct. This would imply that the muscle present in the nerve-muscle construct has a more adult-like phenotype because it is capable of producing more force per gram of muscle tissue.

Providing a functional nerve-muscle interface in vitro in accordance with the construct, system, and method according to the present invention greatly expands the potential to control the phenotype of the muscle tissue in culture and thus expands the usefulness of engineered muscle for virtually all its possible applications.

Turning now to another aspect of the present invention, the suture anchor system described in U.S. Pat. No. 6,207,451 for developing three-dimensional muscle constructs may be replaced with tendon obtained from native tendon tissue or from tendon engineered from fibroblasts in vitro (U.S. Ser. No. 10/602,789) to create a tendon-muscle construct with a functioning myotendinous junction (MTJ).

Self-organized 3-D tendon has been engineered from cells isolated from rat Achilles tendons (U.S. Ser. No. 10/602,789). Primary tendon fibroblasts secrete and organize their own ECM and under the right conditions, and self-assemble into cylindrical constructs without the aid of exogenous scaffolding. The resulting scaffold-free tissue is composed of aligned, small-diameter (50 nm) collagen fibrils, a large number of cells, and an excess of non-collagenous ECM—all characteristics of embryonic tendon. The stress-strain response of the constructs also resembles the non-linear behavior of immature tendons, and the ultimate tensile strength is approximately equal to that of embryonic chick tendon, roughly 2 MPa. These constructs are morphologically and mechanically similar to embryonic tendon and are potentially useful for studying the developmental biology of tendon as well as for clinical use in tendon repair.

The system and method according to the present invention produce 3-D skeletal muscle constructs co-cultured with engineered tendon constructs, or segments of adult (ART) or fetal (FRT) rat-tail tendon. The co-culture of tendon tissue and muscle produces constructs with viable muscle-tendon interfaces that remain intact during force production. The increased expression and localization of two proteins at the MTJ, paxillin and talin, is an indication of the chemical interaction between the tendon and the engineered muscle construct as described below.

According to one aspect of the present invention, muscle tissue may be harvested from female Fischer 344 pregnant rats obtained from Charles River Laboratories, Inc. (Wilmington, Mass.). At day E15 of gestation, surgical procedures are performed to remove the soleus muscles and Achilles and tail tendons from the pregnant rats, and fetal tail from the E15 fetuses. Cells isolated from the soleus muscle and Achilles tendon may be used to fabricate the engineered muscle and tendon constructs, respectively, and adult tails and fetal tails may be used as anchors for tendon-muscle co-cultures. All surgical procedures are performed in an aseptic environment with animals in a deep plane of anesthesia induced using intraperitoneal injections of sodium pentobarbital (65 mg/kg).

The media utilized is as follows. Growth medium (GM) may include 400 mL of HAM F-12 nutrient mixture (Gibco BRL, Carlsbad, Calif.), 100 mL fetal bovine serum (Gibco BRL), and 5 mL anti-biotic anti-mycotic (ABAM, Sigma, St. Louis, Mo.). Differentiation medium (DM) may include 465 mL Dulbecco's modified Eagle medium (DMEM, Gibco BRL), 35 mL 100% horse serum (Gibco BRL), and 5 mL ABAM. The tissue may be dissociated in a dispase and collagenase solution of 20 mL per 2 soleus muscles that includes 8 units of dispase (0.4 units/mg, Sigma) and 200 units of Type 4 collagenase (239 units/mg, Gibco BRL) per mL DMEM. Transport medium (TM) may be prepared in the amount of 5 mL per muscle dissected at the concentration of 2% ABAM in Dulbecco's phosphate-buffered saline (DPBS, Gibco BRL). Pre-incubation medium (PIM) may be prepared in the amount of 3 mL per plate and may include 2.5 mL of 0.05% sodium azide (Sigma, St. Louis, Mo.) in DPBS solution, 22.5 mL differentiation medium, and 0.25 mL ABAM per muscle dissected.

All tissue constructs are engineered in individual (e.g., 35-mm) plates as described previously which serve as a substrate for construct formation. Each plate may be coated with 1.5 mL of SYLGARD® (Type 184 silicon elastomer, Dow Corning Corp., Midland, Mich.) and allowed to cure for ~3 weeks. One week before use, SYLGARD®-treated plates may be coated with laminin, 1.0 mg/cm$^2$ per plate for muscle constructs and 3.0 mg/cm$^2$ for tendon constructs. Natural mouse laminin (Gibco BRL) may be diluted to the appropriate concentration in DPBS pH 7.2, and 3 mL of this solution may be used to coat each plate, which was left to dry for ~48 h. Salt crystals may be dissolved and removed by rinsing the plates with 3 mL DPBS. The plates may then be filled with 2 mL GM and decontaminated using ultraviolet (UV) light (e.g., wavelength 253.7 nm) for ~90 min and placed in a 37 C, 5% carbon dioxide ($CO_2$) incubator for ~1 week before plating muscle cells. For the self-organized tendon constructs, two stainless steel minutien pins (Fine Science Tools, Foster City, Calif.; e.g., 0.20 in diameter) are pinned in spaced apart relationship (~15 mm apart) in each dish. The plates are filled with 1 mL of GM, UV treated for 90 min, and placed in an incubator for ~1 week.

Self-organized tendon (SOT) constructs may be engineered as described previously (U.S. Ser. No. 10/602,789) with modifications. Achilles tendon cells may be isolated by dissociating the tendons in 1 mg/mL type II collagenase (Worthington Biochemical, Lakewood, N.J.) in DMEM plus 2% ABAM. The solution may be placed in an incubator at 37 C (Electron Series II Water Jacketed $CO_2$ Incubator; Thermo Form a Scientific, Waltham, Mass.) overnight to facilitate breakdown of the ECM. After the tissue is dissociated, the cells may be pelleted using centrifugation (AccuSpin FR; Beckman Coulter Inc., Fullerton, Calif.) at 100 g for 5 min, and the supernatant removed using aspiration. The cells are resuspended with GM, expanded in tissue culture dishes (e.g., 100 mm diameter), and then passaged at approximately 60% confluence. Cells are trypsinized between the first and fourth passages, and $2 \times 10^5$ fibroblast cells suspended in 2 mL GM may be seeded onto each plate and supplemented with 100 mg/mL L-ascorbic acid 2-phosphate (Sigma-Aldrich, St. Louis, Mo.), a stable derivative of ascorbic acid. Fresh ascorbic acid may be added each time the GM is changed, such as every 4 days. After approximately 10 to 14 days, DM including DMEM plus 7% fetal bovine serum, 100 mg/mL L-ascorbic acid 2-phosphate, 2 ng/mL transforming growth factor (TGFβ1) (Peprotech Inc., Rocky Hill, N.J.), and 2 mg/mL insulin (Sigma) may be substituted for GM to induce construct formation. The DM is changed every 3 to 4 days, and fresh ascorbic acid, TGFβ1, and insulin may be added each time. Cell layers delaminate after approximately one month, detaching from the substrate and self-organizing to form a construct approximately 15 mm long and 0.5 mm in diameter constrained by the minutien pins. Constructs may then be cut in half and pinned onto monolayers of muscle cells.

For the preparation of muscle and the isolation of satellite cells, both soleus muscles are surgically removed under aseptic conditions, weighed, sterilized in 70% ethanol, and incubated for ~5 min in transport medium. The soleus muscle may be sliced longitudinally, such as into 3 strips. Next, SYLGARD®-treated plates are sterilized in 70% ethanol, and muscle slices are pinned to length, such as 2 muscle strips per plate. Then, 3 mL PIM may be added to each plate, and the plates are UV treated for 90 min. The plates are then placed in a 37 C, 5% $CO_2$ incubator for ~50 h. After the incubation period, muscle slices may be inspected for contamination, and any infected plates discarded. The remaining muscle strips may be removed from the plates and incubated in dispase and collagenase solution (e.g., 2 soleus muscles per 20 mL) in a 37 C shaking water bath for ~4 h. The dissociation may be aided by occasionally shaking each vial slightly by hand. Once the muscle is fully digested (~4 h), the dissociated cells are filtered through a 100-micron filter and centrifuged at 700 g for 10 min at 25 C. Finally, the supernatant is aspirated from the vials, and the pellet resuspended in GM to obtain a concentration of 10 mg of dissociated muscle per 2 mL GM.

After ~1 week of incubation, the GM is aspirated from the previously prepared laminin-coated plates. Without disposing the cells within exogenous scaffolding, 2 mL of the primary muscle cell suspension may be plated onto each culture dish, which is then placed in a 37 C, 5% $CO_2$ incubator for ~5 days. According to one aspect of the present invention, culture plates are not disturbed for at least ~72 h to allow cell adherence to the plates. After ~5 days, GM may be changed every ~48 h until the cells became confluent (approximately 7 days). Once the cells achieve confluence, they may be fed with DM every ~48 h until the myocytes fuse to form multinucleated myotubes that began to contract spontaneously. Approximately two weeks after the plating of the primary muscle cells, tendon tissue may be placed in contact with the muscle cell monolayer. According to one aspect of the present invention, one or more engineered SOT constructs or segments of ART or FRT may be pinned onto the muscle cell monolayer in spaced relationship (e.g., 15 mm apart) (FIG. 10). The pins also serve as anchors to constrain the shape of the developing construct. Approximately 1 week later, the monolayer detaches from the substrate and rolls up to at least partially surround the anchors and form a self-organized, cylindrical muscle-tendon construct.

Seven to 10 days post-construct formation, after approximately 14 to 17 days of co-culture, the muscle-tendon constructs according to the present invention were tested for contractile function and tensile strength. A separate set of specimens was prepared for electron microscopy or histology.

For measuring contractility of the engineered muscle-tendon constructs according to the present invention, the pin on one end of the construct was freed from the SYLGARD® and attached to a force transducer using canning wax. Platinum wire electrodes were positioned on either side of the construct for field stimulation of the entire construct. The temperature of the construct was maintained at ~37±1° C. using a heated aluminum platform. The diameter of the construct was determined and used to calculate cross-sectional area, assuming a circular cross-section. Passive baseline force was measured as the average baseline force preceding the onset of stimulation. Twitches were elicited using a single 1.2-ms pulse at 2.5, 5, 10, and 20 V, whereas maximum tetanic force was determined using a train lasting 1 s and consisting of 1.2-ms pulses at 10V and 10, 20, 40, 60 and 80 Hz. Data files for each peak twitch force and peak tetanic force trace were recorded at 1,000 samples/s and stored for subsequent analysis using LabVIEW (National Instruments, Austin, Tex.). Peak tetanic force was normalized using the cross-sectional area to determine maximum specific force.

After the testing of contractile properties, the tensile strength of each muscle-tendon construct was tested. A tensile tester was custom-built around a Nikon SMZ 800 dissecting microscope outfitted with a Basler A102fc digital video camera (FIG. 2B). Dual actuators were driven by stepper motors (Faulhaber, Clearwater, Fla.) and mounted on crossed roller slides (Del-Tron, Bethel, Conn.). This enables the specimen to stay in the center of view and allows for the determination of true strain. A custom force transducer, designed to have a resolution of 50 mN, was mounted on one of the crossheads. Grips were machined out of stainless steel and placed at the end of both actuators. First the specimen was gripped on each end with a micro artery clamp (Bear/ARO-Surgical, Newport Beach, Calif.), which does minimal damage to the tissue but is able to withstand loading (closing pressure of 40 g for vessels 0.2-0.9 mm in diameter). Then the artery clamp was placed in the larger grips. The stainless steel grips hung into a trough, submerging the specimen in saline. Uniaxial servomotors and data acquisition were controlled using LabVIEW. The samples were loaded at a constant rate until failure, and synchronized force and image recordings were compiled using LabVIEW.

Tendons were harvested from adult and 14-day Fisher rat pups for transmission electron microscopy (TEM). To determine the structural characteristics of the tendon-muscle interface, the specimens were fixed in a 3% formaldehyde-glutaraldehyde buffer solution in 0.1M sodium cacodylate, pH 7.4 (Electron Microscopy Sciences, Fort Washington, Pa.) at 4 C and embedded in Epon (Eponate 12 resin, Ted Pella, Redding, Calif.). For light microscopy, semi-thin sections (1 mm) were cut using an ultramicrotome (Sorvall, Newtown, Conn.), mounted on glass microscope slides, and stained with 1% (w/v) toluidine blue solution (Electron Microscopy Sciences). Ultrathin slices (50 nm) were mounted on uncoated copper grids and stained with aqueous uranyl acetate and lead citrate. The ultrastructure of the samples was investigated using a transmission electron microscope (Philips Medical Systems, Bothell, Wash.) at 60 kV.

For histochemical and immunohistochemical analysis of muscle-tendon structures in vivo and muscle-tendon constructs in vitro, samples were embedded in TBS medium (Triangle Biomedical Sciences, Durham, N.C.) and then sectioned on a cryostat (10 mm, model HM500, Microm, Waldorf, Germany). For immunostaining, sections were incubated in a blocking buffer (20% calf serum in phosphate-buffered saline for 1 h and then in the solution of primary antibody overnight at 4 C. The following primary antibodies were used: mouse anti-paxillin (Upstate, Lake Placid, N.Y.), mouse anti-talin (Sigma), and rabbit anti-collagen Type I (Chemicon International, Temecula, Calif.). Depending on the source of primary antibody, 1-h room temperature incubation with anti-mouse or anti-rabbit Cy3- and Cy2-conjugated secondary antibodies (Jackson ImmunoResearch Lab., West Grove, Pa.) was used for visualization. Nuclei were stained using 5 min incubation with a 40,6-diamidino-2-phenylndole, dilactate (Sigma) in phosphate-buffered saline with Tris (PBST). The sections were observed and photographed through a Zeiss Axiophot-2 microscope (Carl Zeiss, Jena, Germany). For histochemical analysis, sections were stained using Trichrome Masson staining (Sigma).

Values are presented as mean ±standard error. Statistical analysis was performed using Jump In 5.1 (SAS Institute, Inc., Cary, N.C.). A one-way analysis of variance was conducted to compare the differences between constructs. Differences were considered significant at $p<0.05$.

Figure 11A:
FIGS. 11A-B are electron micrographs of adult MTJs taken at two different magnifications showing the highly digitated interface between muscle and tendon.
Figure 11B:
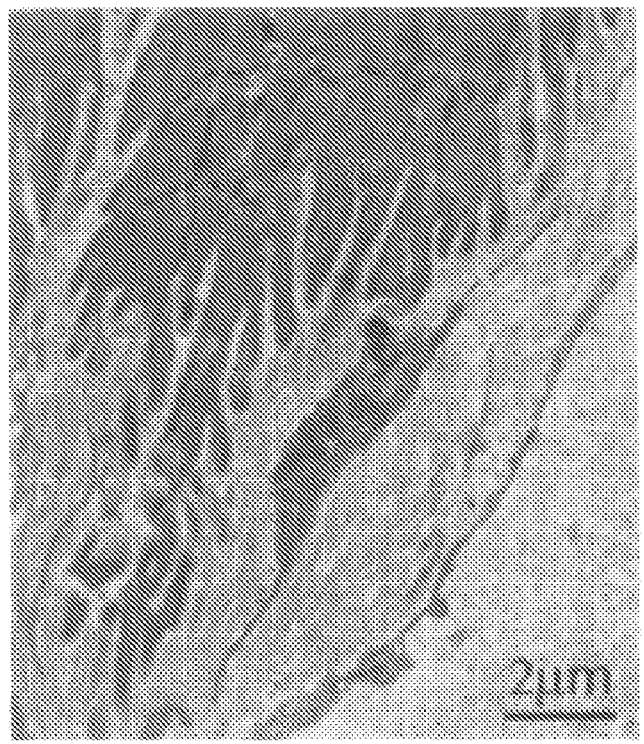
Figure 12:
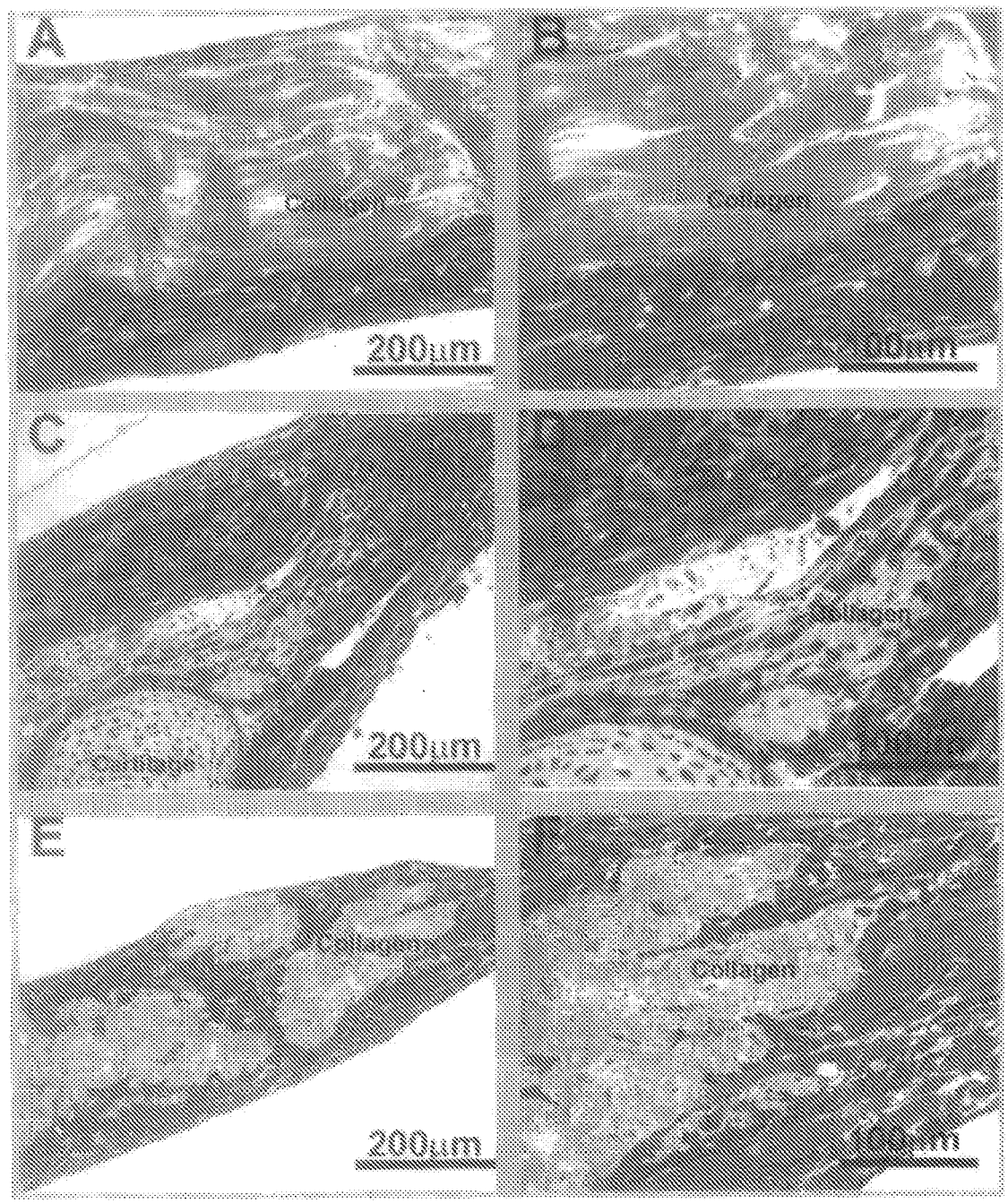
FIGS. 12A-F are semi-thin sections of muscle constructs engineered with anchors comprising (A-B) adult rat tail, (C-D) fetal rat tail, and (E-F) self-organized engineered tendon constructs according to the present invention.

Distinct invaginations of the collagen fibrils from the tendon into the muscle characterize the MTJ of the adult rat tibialis anterior muscle (FIG. 11). At the interface, muscle and tendon form a contiguous interaction of cells. One week after the co-cultured tendon and muscle cells rolled up into a 3-D construct according to the present invention, approximately 14 to 17 days of co-culture, an interface including collagen fibrils (FIG. 12) and myotubes formed and was oriented along the longitudinal axis of the construct. Highly organized collagen fibrils, as seen in adult rats in vivo, characterize the tendon-muscle constructs of the present invention produced from co-culture of the ART with muscle cells (FIGS. 12A-B). Small amounts of collagen in discrete areas of the construct characterize the co-culture of the FRT with the muscle. The presence of cartilage is also indicated, most likely from the developing bones of the FRT. Well-developed areas of collagen characterize the SOT constructs co-cultured with the muscle. In some constructs, the area is continuous, and in others, areas of myotubes and fat cells break up the areas of collagen.

Figure 13A:
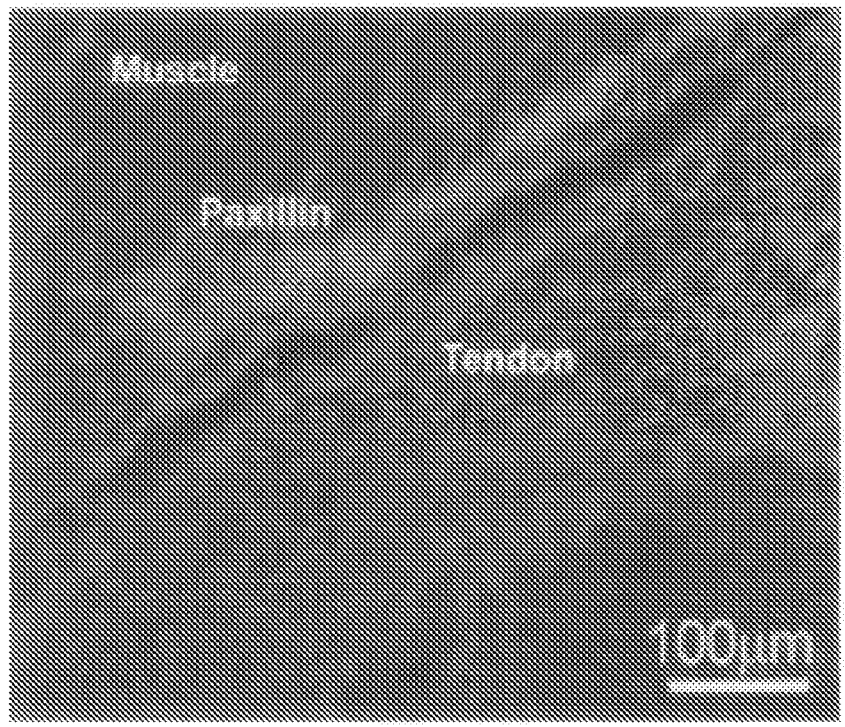
FIGS. 13A-C depict immunostaining for paxillin at the MTJs of neonatal (A) and adult (B) rat muscle, and at the interface of a tendon-muscle construct (C) engineered in vitro using adult rat-tail tendon (ART) according to the present invention.
Figure 13B:
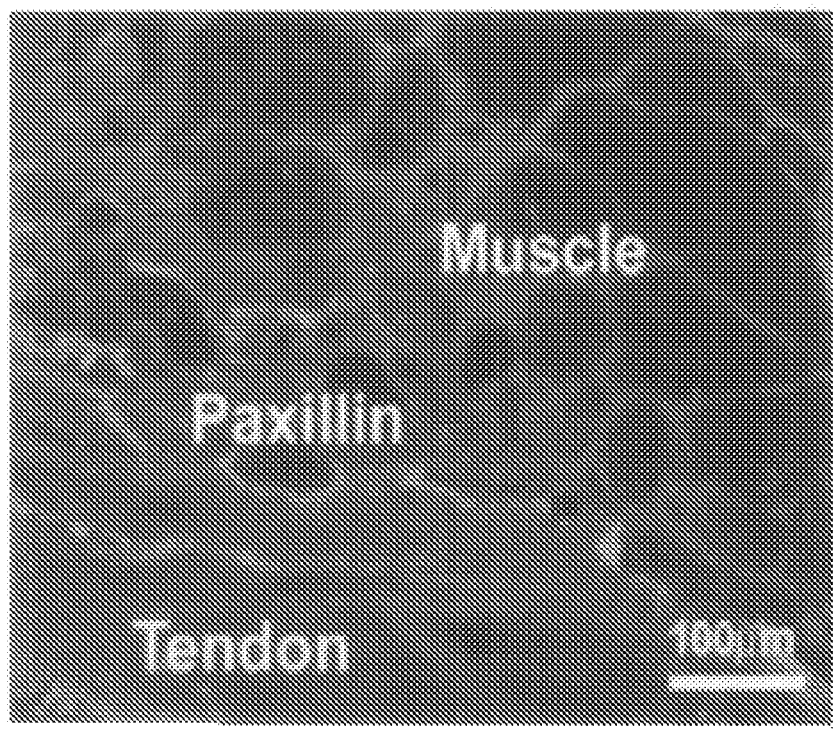
Figure 13C:
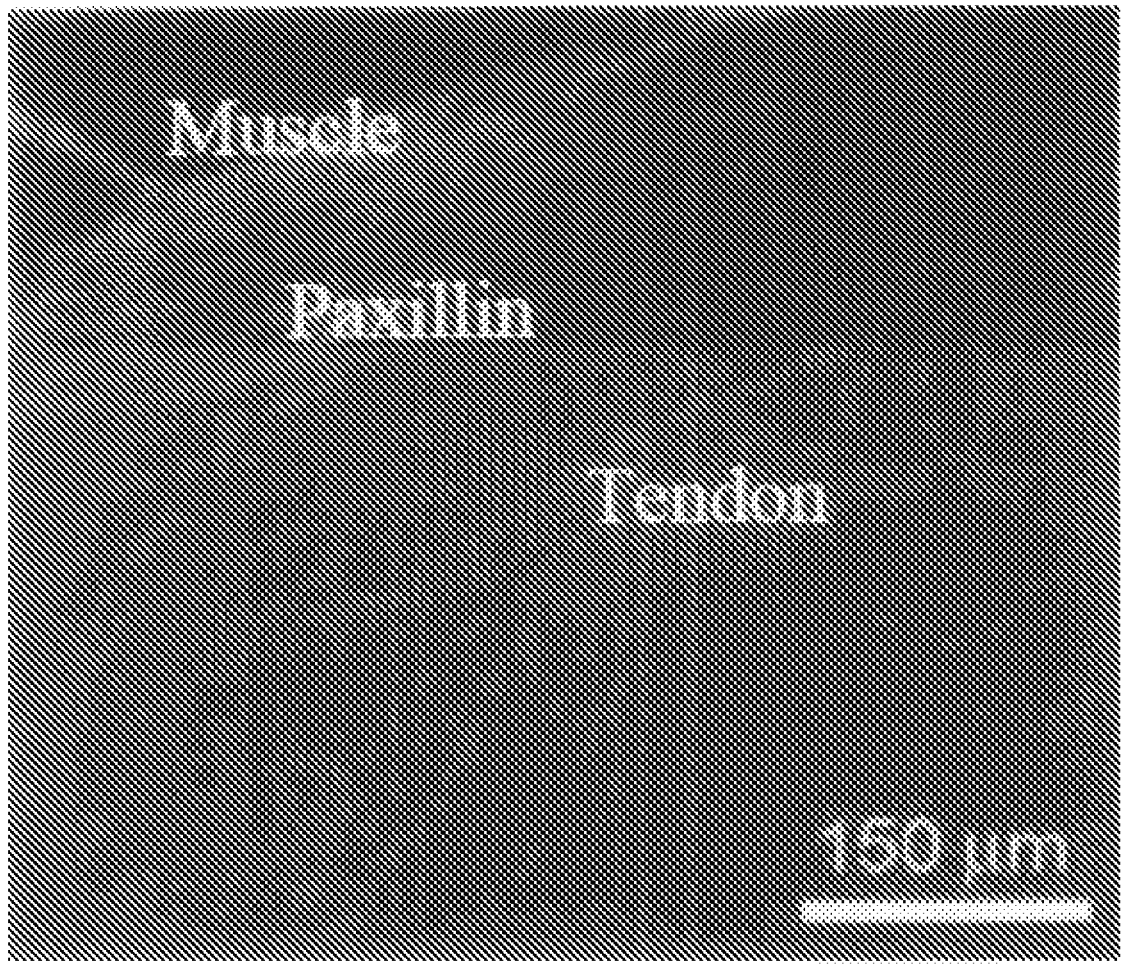

Protein expression at the MTJ was also investigated. The increased expression of several ECM proteins of muscle and tendon including focal adhesion kinase, paxillin, integrin-linked kinase, mitogen-activated protein kinase, and talin has been shown to occur in response to increased mechanical loading of the MTJ. In neonatal tissues, paxillin is expressed in moderate concentrations in the muscle and tendon (FIG. 13A). As the muscle develops, paxillin is preferentially expressed at the neonatal MTJ and is characterized by an increase in the localization between the tendon collagen and muscle (FIG. 13A). In the MTJ of the adult tibialis anterior muscle, paxillin is concentrated at the junction between the collagen fibers and the muscle cells (FIG. 13B). The interface between the ART tendon-muscle constructs according to the present invention looks similar to the neonatal MTJ (FIG. 13C). Paxillin is localized to the interface between the tendon and myotubes. Talin immunohistochemistry showed similar expression and localization to paxillin (results not shown).

Figure 14A:
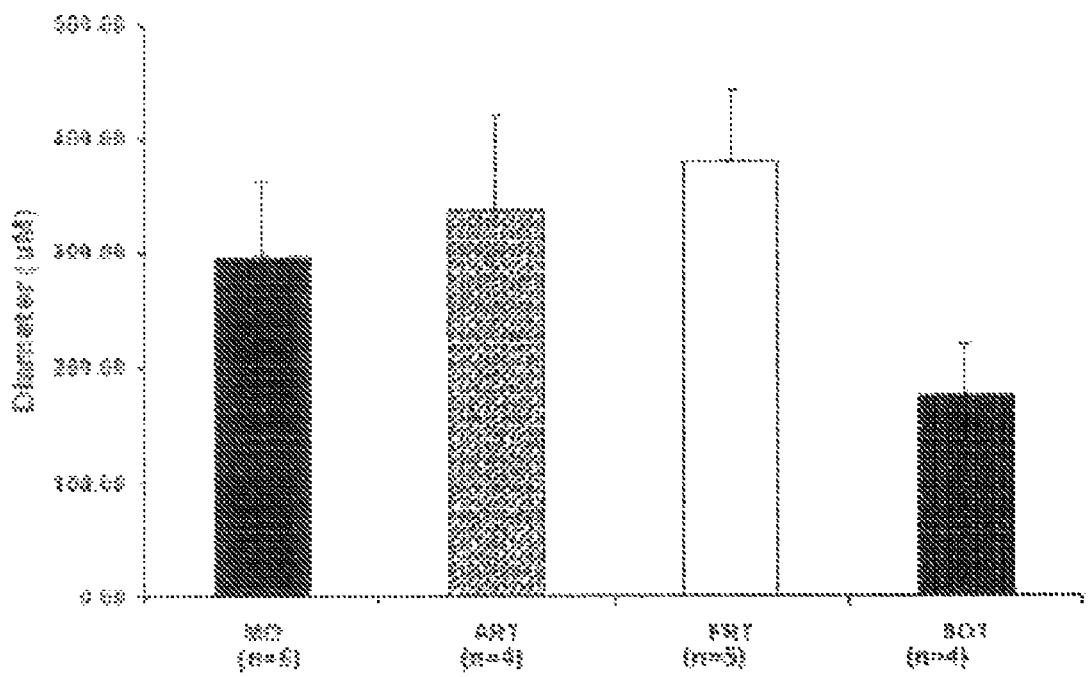
FIGS. 14A-C are graphs of the diameter, maximum isometric force, and specific force, respectively, of muscle-only construct (MO), tendon-muscle constructs (adult rat tail (ART), fetal rat tail (FRT), and engineered self-organized tendon constructs (SOTs) according to the present invention, wherein values are means ±standard errors.
Figure 14B:
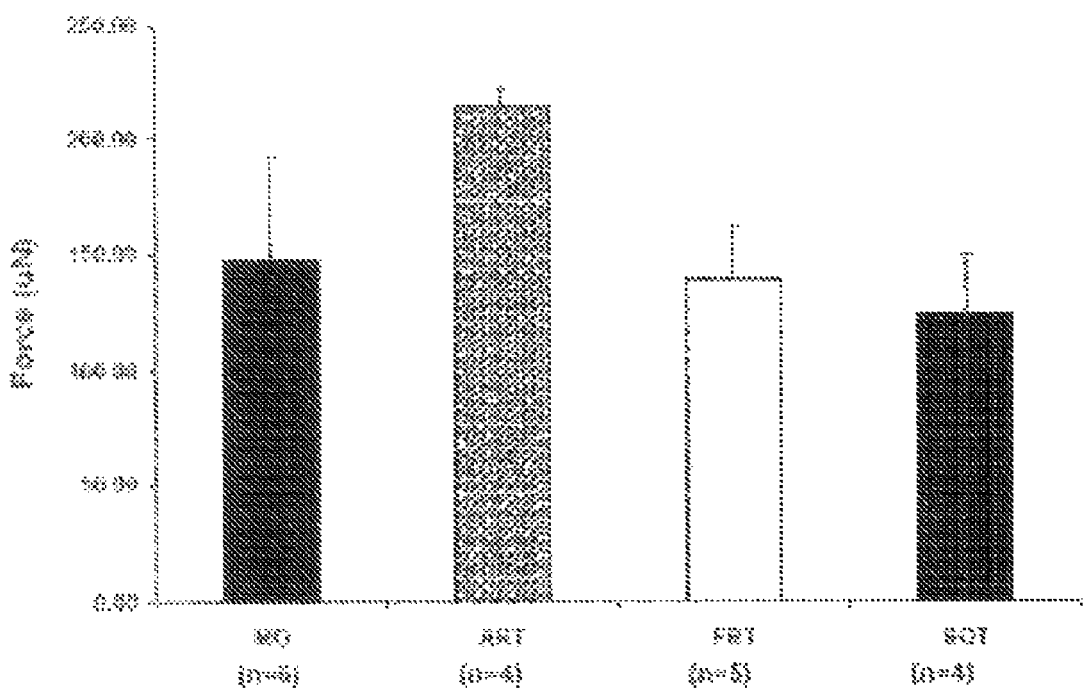
Figure 14C:
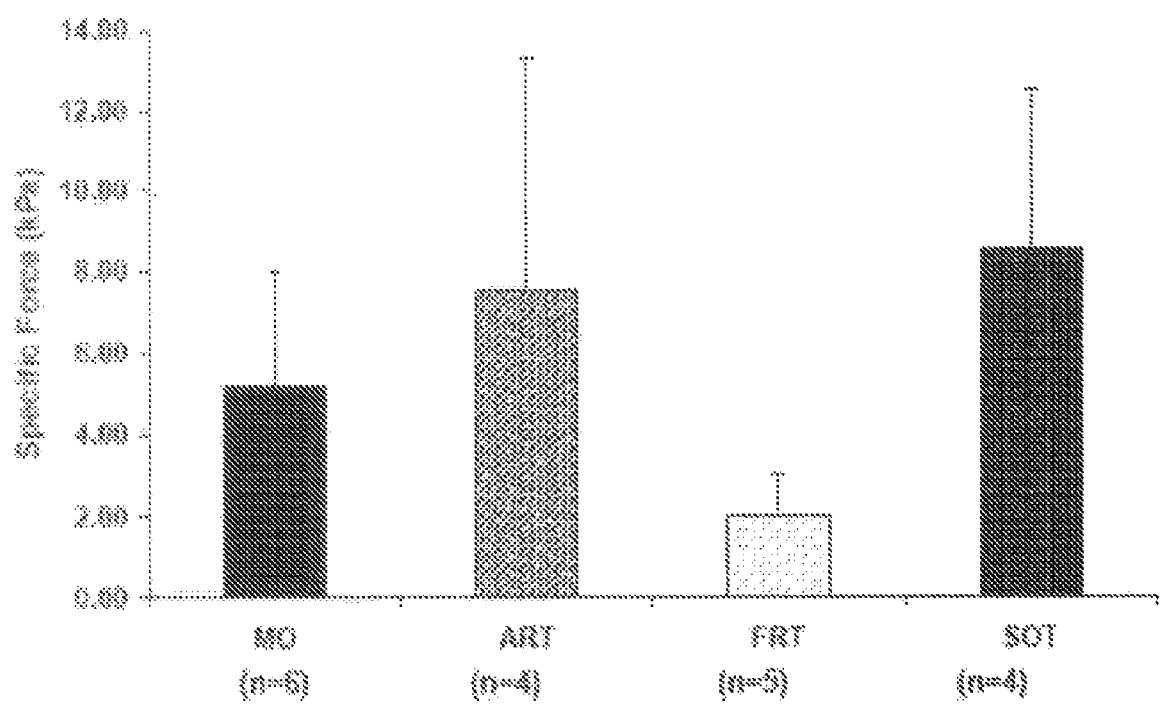

The average diameters (mm), maximum isometric force (mN), and specific force (kPa) of the myooid and tendon-muscle constructs according to the present invention were not significantly different (FIG. 14). There were no significant differences between the diameters or isometric or specific force production of the three tendon-muscle constructs engineered. When the tendon-muscle constructs according to the present invention were subjected to strains of physiological and above-physiological levels, the tendon-muscle interface remained intact and failed at the middle (muscle only) portion of the constructs. The tangent modulus, or passive stiffness, of the constructs was 37.2 kPa±10.3 kPa (n=8).

In accordance with the present invention, three-dimensional tendon-muscle constructs are constructed from co-cultures of myogenic cells, such as from adult soleus muscles, with tendon tissue, such as engineered SOT constructs or segments of ART or E15 FRT. This construct includes a functional MTJ that withstands tensile loading beyond the physiological strain range. At the MTJ of these engineered constructs, there is an increase in the expression and localization of some of the MTJ-specific proteins, such as paxillin, similar to those found in fetal and neonatal MTJs in vivo. Two weeks of co-culture of tendon with the monolayer of myotubes according to the present invention resulted in the formation of MTJs resembling the structure of neonatal MTJs in vivo. The majority of the constructs failed in the midsubstance. The introduction of the tendon to these cultures induces the formation of an interface that morphologically and mechanically resembles a developing MTJ.

The differences in the source and accessibility of the three tendon tissues lends itself to varied advantages for future use. First, the structure of adult tendon is known and tendon tissue can be obtained from the injured donor with the advantage of diminished tissue rejection. While the interface between adult tendon and the engineered muscle construct can withstand the hyperphysiological stresses applied to them, the structure (at least at ten days of co-culture) is not as physiologically advanced as seen in the FRT and SOT constructs. Many engineered tendon constructs can be fabricated from a single biopsy of tendon from an injured donor and should also have diminished rejection upon implantation. The MTJ of a muscle co-cultured with SOT is also more physiologically advanced structurally compared to that of the ART tendon-muscle co-culture. In addition to a structurally and functionally viable interface, the FRT-muscle constructs show the formation of immature cartilage and bone.

Current literature suggests that the transmission of force between myofibrils and the ECM occurs via 2 parallel systems that link intracellular and extracellular structural proteins: the dystrophin-diphosphoglycerate system and the integrin system. The integrins create mechanical links from the ends of the myofibrils by binding actin filaments on the cytoplasmic side and one or more ECM molecules, including vinculin, FAK, paxillin, and talin, on the extracellular side, thus creating a system for longitudinal transmission of force (Bockholt et al., *Exp Cell Res* 203: 39, 1992; Turner and Burridge, *Curr Opin Cell Biol* 3: 849, 1991; Turner et al., *Exp Cell Res* 192: 651, 1991; Tidball et al., *J Cell Biol* 103: 1465, 1986; Chen et al., *J Biol Chem* 270: 16995, 1995). It has been suggested that the integrin system is the sensor of tensile strain and elicits electrical or chemical signals that are proportional to the strains they experience. Paxillin has been shown to interact with many cytoskeletal proteins, suggesting that paxillin is a focal adhesion scaffolding protein, which it has been postulated may play a role in integrin-mediated adhesion and focal adhesion dynamics (Turner, *J Cell Sci* 113 Pt 23: 4139, 2000; Schaller, *Biochim Biophys Acta* 1540:1, 2001). Therefore, the expression of paxillin, one of the proteins involved in the integrin system, suggests that the tendon-muscle constructs according to the present invention are experiencing the required tensile stress to invoke expression, localization, and formation of MTJ-like structures.

In the hindlimb muscles of rats, the focal adhesion complex proteins such as paxillin can adapt to the mechanical loading state of the muscle (Gordon et al., J Appl Physiol 90: 1174, 2001). Paxillin is expressed in the muscle and tendon in embryonic limb tissues. As mechanical stress is applied to the MTJ, paxillin localizes to the interface between the muscle and tendon. More-diffuse banding of paxillin may be noted in the neonatal sample than in the adult sample in FIG. 13. In the ART sample, paxillin is expressed in the muscle area of the construct, and localization of paxillin occurs at the muscle-tendon interface. Expression of paxillin in the tendon area of the ART construct is not seen. This indicates that the muscle portion of the construct contains undeveloped myofibers and that the construct is experiencing some mechanical stress that is signaling the paxillin to localize at the muscle-tendon interface. The tendon-muscle constructs were studied 8 days after they obtained their 3-D structure, which was approximately 25 days after initial plating of cells. It could be that the engineered constructs need more time to form the structural elements of the MTJ or that the constructs are not experiencing enough (cyclic) load-bearing strain to achieve an adult-like MTJ phenotype. Therefore, the time in culture may be increased and cyclic mechanical loading may be introduced to affect the structure and function of the engineered constructs.

Therefore, using three sources of tendon tissue, the system and method according to the present invention are capable of successfully engineering 3-D, self-organizing, scaffold-less muscle-tendon constructs with viable MTJs characterized by structural features and protein expression patterns similar to those found in neonatal MTJs developed in vivo. Tensile tests on the three different muscle-tendon co-cultures demonstrate that they have the structural integrity to withstand hyperphysiological mechanical strains. The creation of an engineered musculoskeletal tissue with a functional tendon-muscle interface in vitro according to the present invention greatly expands the potential to control the phenotype of the muscle tissue in culture, and thus expands the usefulness of the engineered muscle as a model for developmental muscle biology, muscle pharmacology, and for transplantation of diseased or damaged muscle.

The creation of engineered musculoskeletal tissue with functional myotendinous (MTJ) and neuromuscular (NMJ) junctions will not only restore the function of complex tissues such as muscle, tendon, and nerve following traumatic injury, but can also be used as a model for studying developmental muscle biology and muscle pharmacology. According to the present invention, the co-culture of tendon or neural tissue with engineered muscle tissue produces constructs with viable myotendinous interfaces that remain intact during force production, and viable neuromuscular interfaces that advance the phenotype of the muscle tissue within the construct. Of course, three-dimensional (3-D) engineered tissues containing both myotendinous and neuromuscular interfaces, two of the principal tissue interfaces required for a functional musculoskeletal construct, can also be constructed in accordance with the present invention.

Engineered muscle constructs contain embryonic and neonatal MHC ready for the proper cues to develop into highly organized and functionally active structures. The environment of the engineered constructs according to the present invention may be manipulated with electrical stimulation to shift the MHC isoform from neonatal to the adult and to fabricate a construct with adult phenotype. The type of activity a muscle is exposed to is driven by its innervation. Innervation by slow motor neurons leads to a slow MHC isoform and lower isometric force production, compared with innervation of fast motor neurons which leads to expression of the fast MHC isoform and greater maximum isometric force production. The following two stimulation protocols may be used: "slow" (20 Hz train of 5 pulses with a rest pause of 3.75 seconds between pulse trains) and "fast" (100 Hz train of 5 pulses, with a 100 second rest pause between pulse trains). The electrical stimulation may be applied using paired bipolar pulses, with a pulse width of 1.5 ms and amplitude of 5V. An increase in the number of NMJs in conjunction with applied electrical activity in vitro may lead to a more advanced phenotype in the muscle and tendon, increased force production in the engineered muscles, and stronger and more developed tissue interfaces.

Figure 15A:
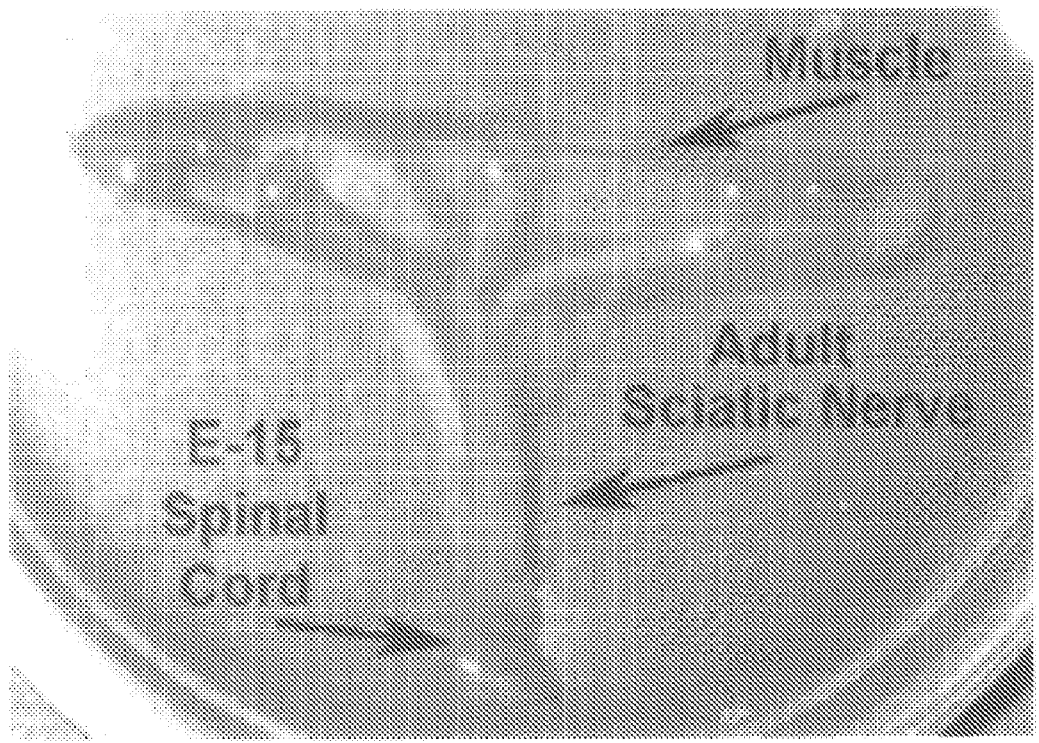
FIGS. 15A-B are photographs of the co-culture of a muscle-tendon construct with sciatic nerve from adult rat (A) and neonatal rat (B) with E-15 fetal rat spinal cord explant pinned to distal end of sciatic nerve according to the present invention.
Figure 15B:
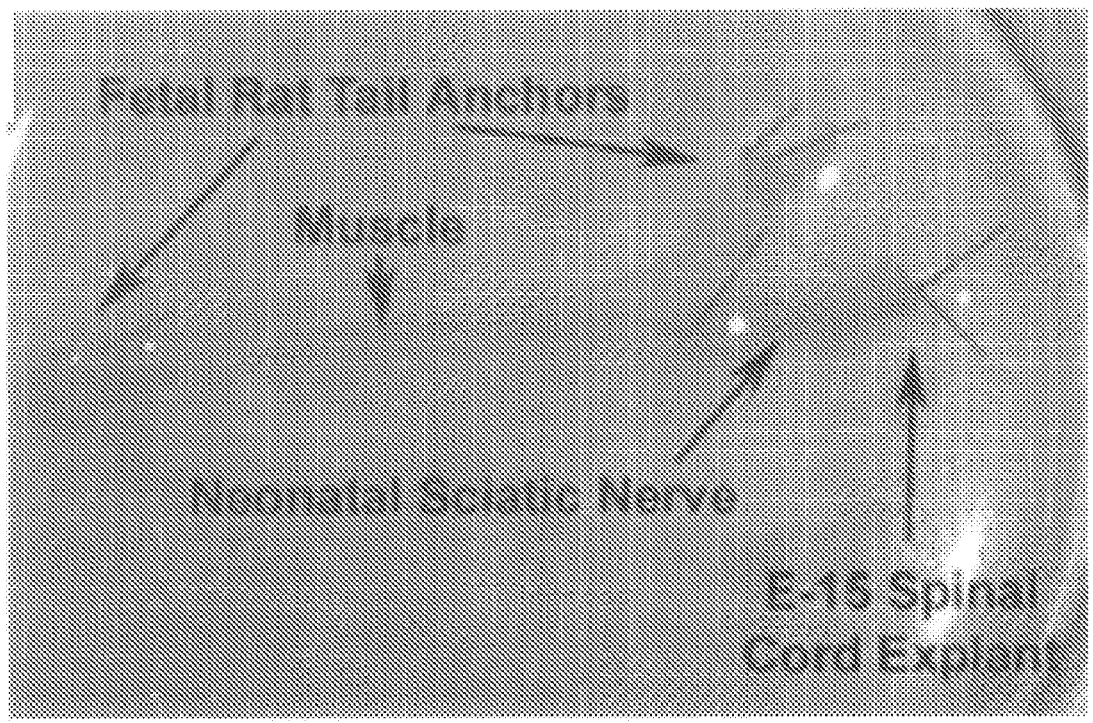
Figure 15C:
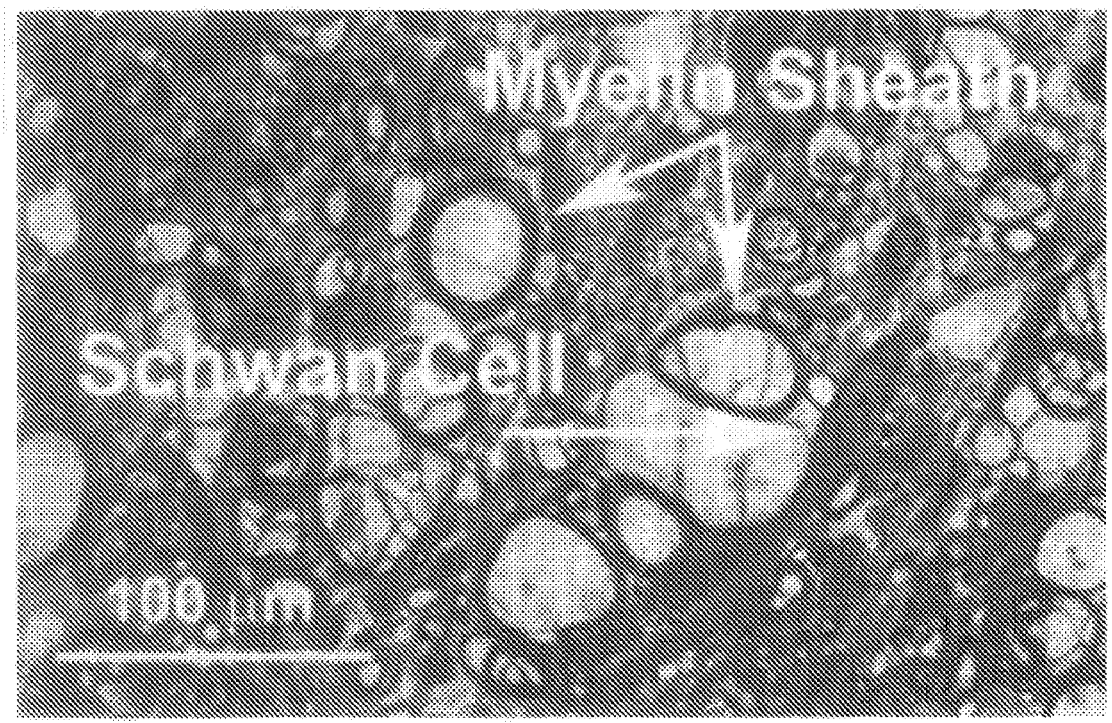
FIGS. 15C-D are semi-thin sections of adult sciatic nerve after one month co-culture with a muscle-tendon construct according to the present invention indicating the presence of viable myelin sheaths surrounded by Schwann cells (C) wherein the majority of the myelin sheaths are empty (red arrows) with a few myelin sheaths with viable neurons (black arrows) (D)
Figure 15D:
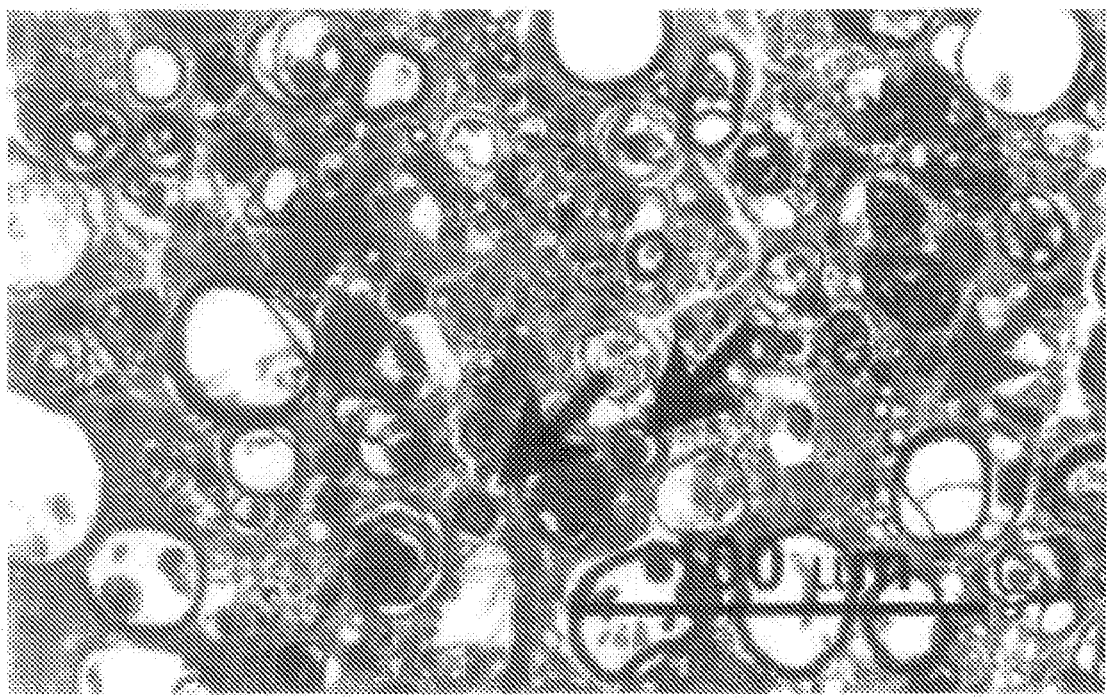

In further accordance with the present invention, a synthetic, engineered, or tissue-based nerve conduit may be used to direct nerve growth towards the muscle construct, thus increasing the innervation ratio of the construct. Conduits such as, but not limited to, silicone tubing, synthetic polymers, and neonatal sciatic nerve may serve to induce the concerted migration of neural extensions from E15 spinal cord explants or other neural tissue towards the construct. For example, sciatic nerve from adult rats can serve as a conduit for directing growth of neural extensions to an engineered construct (FIG. 15A). Sciatic nerve from 4 day old neonatal rat pups is an alternative conduit for directing the growth of neural extensions (FIG. 15B). Both viable myelin sheaths and schwann cells have been observed after one month of co-culture with a muscle-tendon construct (FIG. 15C). A percentage of the myelin sheaths have either neurons which have not degraded in co-culture to new neurons that have migrated off of the fetal spinal cord explant down the sciatic nerve conduit (FIG. 15D).

The development of the mechanical properties of muscle, tendon, and the MTJ is reliant upon the innervation of muscle fibers during development. The absence of innervation hinders the structural development of muscle and tendon. The system and method of nerve-muscle co-culture according to one aspect of the present invention creates random neural extensions some of which can be electrically stimulated to elicit a force response from a small number of muscle fibers within the construct. The use of a conduit to direct the neural extensions either to or from the construct may group the neural extensions and increase the innervation ratio and the ability to recruit more muscle fibers within the muscle construct to produce force. The neural extensions within the conduit could also be sutured to a nerve in vivo during implantation.

According to the present invention, the expression of neurotrophic proteins like glial derived neurotrophic factor (GDNF) may be increased to enhance the construct's attractiveness for outgrowing neurites. In particular, the transfection of the myotubes with Myo-GDNF-containing plasmid prior to forming a 3-D structure may increase GDNF secretion and attract E-15 neuronal sprouts toward the construct via the conduit. Overexpression of GDNF in the muscle cells of the constructs according to the present invention can regulate the number of innervating axons. The enhancement of the interaction between the nerve-muscle construct and nerve shunts may further drive the advancement of the construct to a more adult-like phenotype.

Figure 16A:
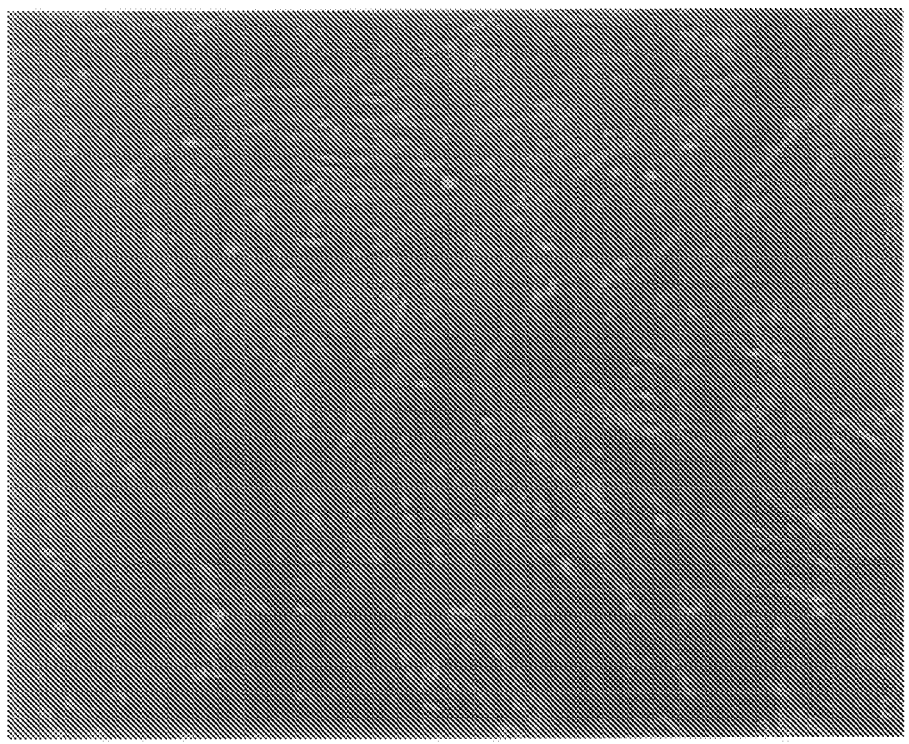
FIGS. 16A-B depict monolayers of myoblasts (A) and myotubes (B) over-expressing GDNF with GFP as a marker of transfection efficiency.
Figure 16B:

Using a MyoGDNF plasmid, approximately 90% of the myoblasts in the cell culture were successfully transfected with the MyoGDNF. Myoblasts were co-transfected with a GFP plasmid for estimating the efficiency of the transfection (FIG. 16). Differentiation from myoblast to myotube does not alter the plasmid-induced GDNF expression in the cell culture system according to the present invention. The transfection of the myotubes with Myo-GDNF-containing plasmid prior to forming a 3-D structure may increase GDNF secretion and attract E-15 neuronal sprouts toward the construct via the conduit. The myotubes in the constructs may be transfected with a MyoGDNF plasmid that over-expresses GDNF under a muscle-specific (myogenin) promoter (Nguyen et al., *Science,* 279:1725, 1998). The myogenin promoter may be used because it drives transgene expression in muscle beginning in embryogenesis, about the time axons first approach muscle fibers, and continues expression into postnatal life (Cheng et al., *Exp Brain Res,* 104: 199, 1995).

Figure 17A:
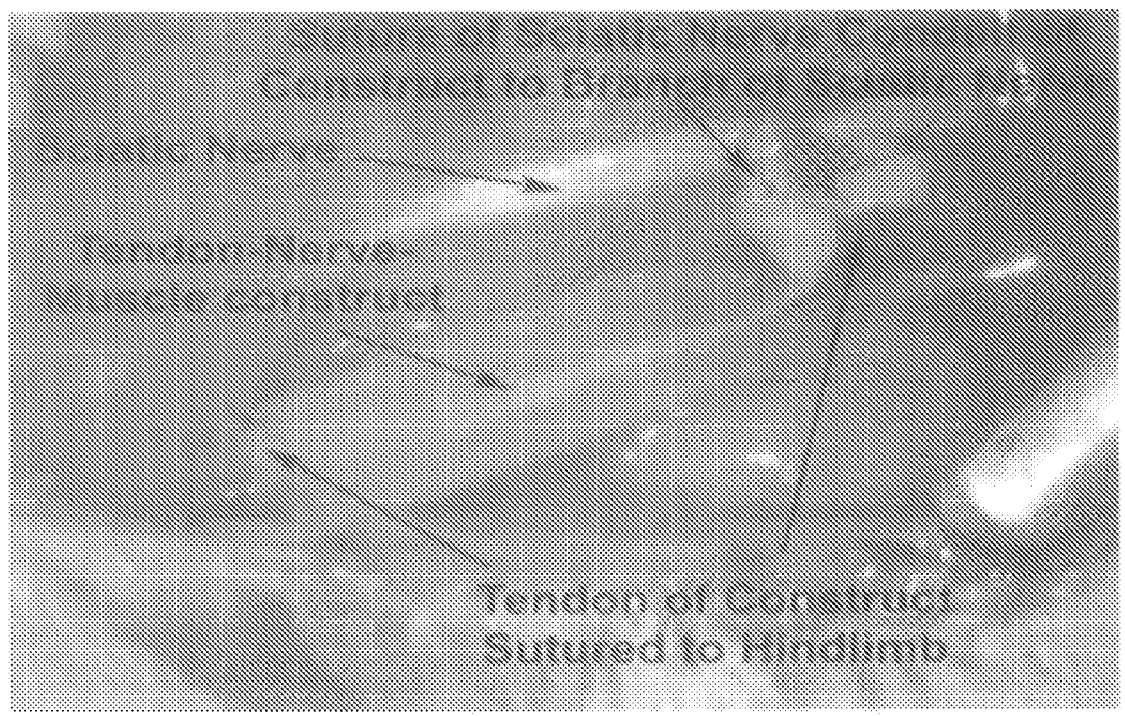
FIGS. 17A-B are photographs illustrating the implantation of engineered constructs into a host animal with tension and innervation at the time of implantation (A) and after 30 days of implantation (B).
Figure 17B:
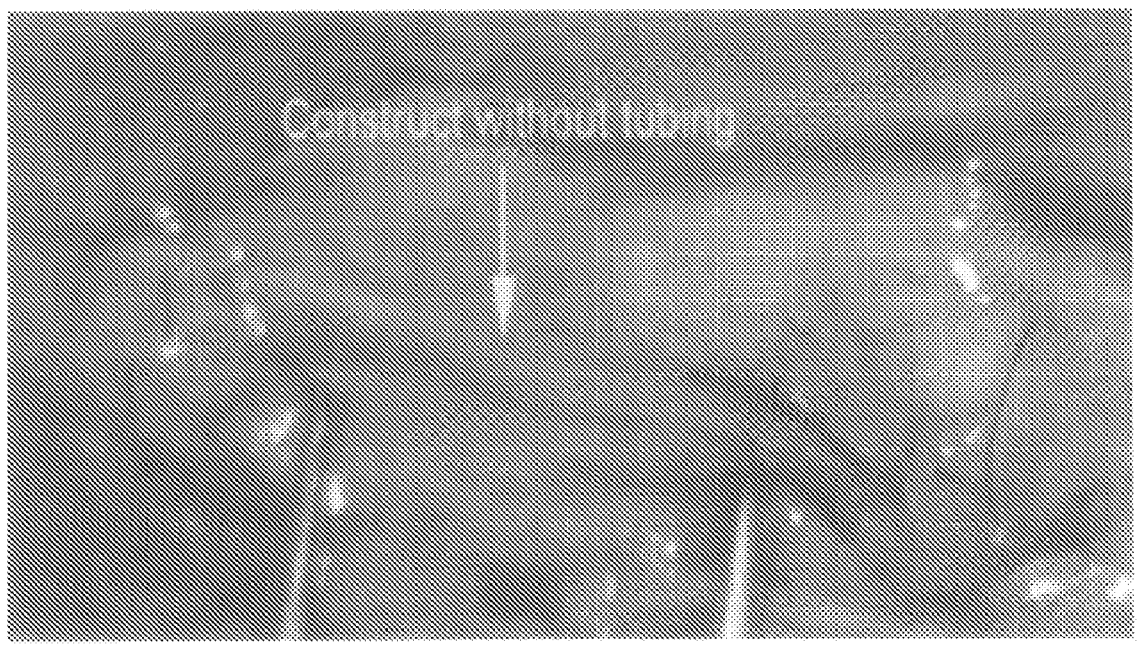

Muscle-tendon constructs according to the present invention were implanted using tension induced by suturing the tendon anchor of the construct to the hindlimb of the rat plus innervation from a branch of the sciatic nerve through a nerve conduit (FIG. 17A). After 30 days of implantation, this construct had become highly vascularized and was surrounded by a thin sheath of connective tissue, wherein the construct was indistinguishable from surrounding muscle (FIG. 17B). The diameter of the construct was 2.8 fold bigger (700 microns) than the average in vitro construct and the maximum force produced by in vitro field stimulation was 3.5 times greater than nerve-muscle in vitro constructs.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A skeletal muscle construct, comprising:
   primary muscle cells provided on a substrate without disposing the cells within an exogenous scaffold, the cells cultured in vitro such that the cells form a confluent monolayer constrained by at least two anchors secured thereto; and
   at least one secondary tissue provided in contact with the monolayer such that the monolayer detaches from the substrate and self-organizes to at least partially surround the at least one secondary tissue, thereby forming a three-dimensional skeletal muscle construct having a functional interface with the secondary tissue, wherein the secondary tissue includes neural tissue such that the interface includes a neuromuscular interface.

2. The construct according to claim 1, wherein the interface includes neural cells fused with myotubes.

3. The construct according to claim 1, wherein the interface includes acetylcholine receptors.

4. A skeletal muscle construct, comprising:
   primary muscle cells provided on a substrate without disposing the cells within an exogenous scaffold, the cells cultured in vitro such that the cells form a confluent monolayer constrained by at least two anchors secured thereto; and
   at least one secondary tissue provided in contact with the monolayer such that the monolayer detaches from the substrate and self-organizes to at least partially surround the at least one secondary tissue, thereby forming a three-dimensional skeletal muscle construct having a functional interface with the secondary tissue, wherein the secondary tissue includes tendon tissue such that the interface includes a myotendinous interface.

5. The construct according to claim 4, wherein the interface includes organized collagen fibrils.

6. The construct according to claim 4, wherein the interface expresses at least one myotendinous junction-specific protein.

7. A skeletal muscle construct, comprising:
   primary muscle cells provided on a substrate without disposing the cells within an exogenous scaffold, the cells cultured in vitro such that the cells form a confluent monolayer constrained by at least two anchors secured thereto; and
   at least one secondary tissue provided in contact with the monolayer such that the monolayer detaches from the substrate and self-organizes to at least partially surround the at least one secondary tissue, thereby forming a three-dimensional skeletal muscle construct having a functional interface with the secondary tissue, wherein the secondary tissue includes neural tissue and tendon tissue such that the interface includes a neuromuscular interface and a myotendinous interface.

8. A method for forming a skeletal muscle construct, comprising:
   providing primary muscle cells on a substrate without disposing the cells within an exogenous scaffold;
   culturing the cells in vitro such that the cells form a confluent monolayer;
   securing at least two anchors to the monolayer in spaced relationship; and
   providing at least one secondary tissue in contact with the monolayer such that the monolayer detaches from the substrate and self-organizes to at least partially surround the at least one secondary tissue, thereby forming a three-dimensional skeletal muscle construct having a functional interface with the secondary tissue, wherein providing the secondary tissue includes providing neural tissue such that the interface includes a neuromuscular interface.

9. The method according to claim 8, further comprising directing growth of the neural tissue toward the construct via a conduit.

10. The method according to claim 8, wherein forming the skeletal muscle construct having a functional interface with the neural tissue alters the myosin heavy chain profile toward an adult phenotype.

11. The method according to claim 8, further comprising electrically stimulating the construct to shift the myosin heavy chain isoform.

12. The method according to claim 8, further comprising transfecting myotubes in the monolayer with a Myo-GDNF-containing plasmid.

13. A method for forming a skeletal muscle construct, comprising:
   providing primary muscle cells on a substrate without disposing the cells within an exogenous scaffold;
   culturing the cells in vitro such that the cells form a confluent monolayer;
   securing at least two anchors to the monolayer in spaced relationship; and
   providing at least one secondary tissue in contact with the monolayer such that the monolayer detaches from the substrate and self-organizes to at least partially surround the at least one secondary tissue, thereby forming a three-dimensional skeletal muscle construct having a functional interface with the secondary tissue, wherein providing the secondary tissue includes providing tendon tissue such that the interface includes a myotendinous interface.

14. The method according to claim 13, further comprising electrically stimulating the construct to shift the myosin heavy chain isoform.

15. The method according to claim 13, further comprising transfecting myotubes in the monolayer with a Myo-GDNF-containing plasmid.

16. A method for forming a skeletal muscle construct, comprising:
   providing primary muscle cells on a substrate without disposing the cells within an exogenous scaffold;
   culturing the cells in vitro such that the cells form a confluent monolayer;
   securing at least two anchors to the monolayer in spaced relationship; and
   providing at least one secondary tissue in contact with the monolayer such that the monolayer detaches from the substrate and self-organizes to at least partially surround the at least one secondary tissue, thereby forming a three-dimensional skeletal muscle construct having a functional interface with the secondary tissue, wherein providing the secondary tissue includes providing neural tissue and tendon tissue such that the interface includes a neuromuscular interface and a myotendinous interface.

17. The method according to claim 16, further comprising electrically stimulating the construct to shift the myosin heavy chain isoform.

18. The method according to claim 16, further comprising transfecting myotubes in the monolayer with a Myo-GDNF-containing plasmid.

* * * * *